US009274122B2

(12) United States Patent
Varadi et al.

(10) Patent No.: US 9,274,122 B2
(45) Date of Patent: Mar. 1, 2016

(54) METHODS FOR DETERMINING ACTIVE INGREDIENTS IN PRO-DRUG PEG PROTEIN CONJUGATES WITH RELEASABLE PEG REAGENTS (IN VITRO DE-PEGYLATION)

(75) Inventors: Katalin Varadi, Vienna (AT); Gerald Schrenk, Vienna (AT); Hanspeter Rottensteiner, Vienna (AT); Peter Turecek, Klosterneuburg (AT); Alfred Weber, Vienna (AT); Heinz Anderle, Klosterneuburg (AT); Sean M. Culbertson, Gurley, AL (US); Zhihao Fang, Madison, AL (US); Harold Zappe, Harvest, AL (US); Ping Zhang, Millbrae, CA (US); Mary J. Bossard, Madison, AL (US)

(73) Assignees: BAXALTA INCORPORATED, Bannockburn, IL (US); BAXALTA GMBH, Glattpark (Opfikon) (CH); NEKTAR THERAPEUTICS, San Francisco, CA (US)

( * ) Notice: Subject to any disclaimer, the term of this patent is extended or adjusted under 35 U.S.C. 154(b) by 856 days.

(21) Appl. No.: 12/582,497

(22) Filed: Oct. 20, 2009

(65) Prior Publication Data

US 2010/0112607 A1 May 6, 2010

Related U.S. Application Data

(60) Provisional application No. 61/107,257, filed on Oct. 21, 2008, provisional application No. 61/242,634, filed on Sep. 15, 2009.

(51) Int. Cl.
| | |
|---|---|
| *G01N 33/53* | (2006.01) |
| *C07K 14/00* | (2006.01) |
| *G01N 33/68* | (2006.01) |
| *G01N 33/542* | (2006.01) |
| *G01N 33/58* | (2006.01) |
| *G01N 33/86* | (2006.01) |

(52) U.S. Cl.
CPC .............. *G01N 33/68* (2013.01); *G01N 33/542* (2013.01); *G01N 33/582* (2013.01); *G01N 33/86* (2013.01); *G01N 2333/76* (2013.01)

(58) Field of Classification Search
None
See application file for complete search history.

(56) References Cited

U.S. PATENT DOCUMENTS

| | | | | |
|---|---|---|---|---|
| 4,877,608 A | * | 10/1989 | Lee et al. .................... | 424/176.1 |
| 5,824,784 A | | 10/1998 | Kinstler et al. | |
| 6,515,100 B2 | | 2/2003 | Harris | |
| 7,122,189 B2 | | 10/2006 | Zhao et al. | |
| 7,259,224 B2 | | 8/2007 | Harris et al. | |
| 7,267,941 B2 | | 9/2007 | Snell et al. | |
| 2004/0022792 A1 | * | 2/2004 | Klinke et al. .............. | 424/178.1 |
| 2005/0276823 A1 | * | 12/2005 | Cini et al. ...................... | 424/400 |
| 2006/0160948 A1 | | 7/2006 | Scheiflinger et al. | |
| 2006/0183682 A1 | * | 8/2006 | Juul-Mortensen ............. | 514/12 |
| 2006/0293499 A1 | * | 12/2006 | Bentley et al. ................ | 528/322 |
| 2008/0234193 A1 | * | 9/2008 | Bossard et al. ................ | 514/12 |

FOREIGN PATENT DOCUMENTS

| | | | |
|---|---|---|---|
| JP | 2000-515542 A | | 11/2000 |
| WO | WO-98/05361 A2 | | 2/1998 |
| WO | WO-2004/089280 | | 10/2004 |
| WO | WO 2004089280 A2 | * | 10/2004 |
| WO | WO-2006/071801 | | 7/2006 |
| WO | WO-2006/138572 | | 12/2006 |
| WO | WO-2007/025988 | | 3/2007 |
| WO | WO 2008082669 A2 | * | 7/2008 |

OTHER PUBLICATIONS

Bedu-Addo, AAPS PharmSci, 2002.*
Adibi, Journal of Applied Physiology, 25, 1, 1968.*
Bedu-Addo et al., Preformulation development of recombinant pegylated staphylokinase SY161 using statistical design. *AAPA Pharmsci* 4(4) Article 19: 1-13 (2002).
Caliceti, Pharmacokinetic and biodistribution properties of poly(ethylene glycol)-protein conjugates. *Adv. Drug Deliv. Rev.* 55:1261-77 (2003).
Greenwald et al. Drug delivery system employing 1,4- or 1,6-elimination: Poly(ethylene glycol) prodrugs of amine-containing compounds. *J. Med. Chem.* 42:3657-67 (1999).
Nesher et al., Reversible pegylation prolong the hypotensive effect of atrial natriuretic peptide. *Bioconjugate Chem.* 19:342-8 (2008).
Ouchi et al., Design of antitumor agent-terminated poly(ethylene glycol) conjugate as macromolecular progrug. *Polymer Preprints* 38:582-3 (1997).
Perlman, Glycosylation of an N-terminal extension prolongs the half-life and increases the in vivo activity of follicle stimulating hormone. *J. Clin. Endo. Metab.* 88:3227-35 (2003).
Pitkin, Charge and lipophilicity govern the pharmacokinetics of glycopeptide antibodies. *Antimicrob. Ag. Chemo.* 29:440-4 (1986).
Roberts et al., Attachment of degradable poly(ethylene glycol) to proteins has the potential to increase therapeutic efficacy. *J. Pharmaceutical Assoc.* 87:1440-5 (1987).

(Continued)

*Primary Examiner* — Robert A Wax
*Assistant Examiner* — William Craigo
(74) *Attorney, Agent, or Firm* — Marshall, Gerstein & Borun LLP

(57) ABSTRACT

The invention relates to the development of in vitro assay systems that force the release of a water-soluble polymer, such as polyethylene glycol (PEG) and polysialic acid (PSA), from proteins modified with a reversibly-linked water-soluble polymer. The invention includes methods for analyzing the release of the water-soluble polymer and measuring regained protein activity. The invention further includes methods appropriate for the quality control of proteins modified with releasable water-soluble polymers, including polymers like PEG and PSA.

19 Claims, 11 Drawing Sheets

(56) References Cited

OTHER PUBLICATIONS

Shechter et al., Reversible pegylation of insulin facilitates its prolonged action in vivo. *Eur. J. Pharmaceutics Biopharm.* 70:19-28 (2008).

Tsubery et al., Prolonging the action of protein and peptide drugs by a novel approach of reversible polyethylene glycol modification. *J. Biol. Chem.* 279:38118-24 (2004).

Vehaskari, Glomerular charge and urinary protein excretion: Effects of systemic and intrarenal prolycation infusion in the rat. *Kidney Intl.* 22:127-35 (1982).

International Search Report and Written Opinion of the International Searching Authority, PCT/US2009/061327, European Patent Office, dated Apr. 7, 2010.

Extended European Search Report for European Patent Application No. EP11009919, European Patent Office, dated Feb. 2, 2012.

\* cited by examiner

METHODS FOR DETERMINING ACTIVE INGREDIENTS IN PRO-DRUG PEG PROTEIN CONJUGATES WITH RELEASABLE PEG REAGENTS (IN VITRO DE-PEGYLATION)

RELATED APPLICATIONS

This application claims benefit of U.S. Provisional Patent Application Ser. No. 61/107,257, filed Oct. 21, 2008, and U.S. Provisional Patent Application Ser. No. 61/242,634, filed Sep. 15, 2009, each of which is incorporated herein by reference in its entirety.

FIELD OF THE INVENTION

The invention generally relates to the development of in vitro assay systems to force the release of a water-soluble polymer, such as polyethylene glycol (PEG) and polysialic acid (PSA), from proteins modified with a reversibly-linked water-soluble polymer. The invention includes methods for analyzing the release of the water-soluble polymer and measuring regained protein activity. The invention further includes methods appropriate for the quality control of proteins modified with releasable water-soluble polymers, including polymers like PEG and PSA.

BACKGROUND OF THE INVENTION

The lack or dysfunction of blood clotting Factor VIII (FVIII) is associated with the bleeding disorder hemophilia A. The treatment of choice for the management of hemophilia A is replacement therapy with plasma-derived or recombinant FVIII (rFVIII) concentrates. It is generally accepted that patients with severe hemophilia A, i.e. with FVIII levels below 1%, are best treated by a prophylactic therapy with the aim of keeping FVIII levels above 1% in-between doses. Taking into account the average half-lives of the various FVIII products in the circulation, this circulating concentration can usually be achieved by administering FVIII two to three times a week. To increase the convenience of current prophylaxis therapy, the development of a next generation product with enhanced pharmacodynamic and pharmacokinetic properties, while maintaining all other product characteristics, is envisaged to allow dosing on a weekly basis.

Therapeutic polypeptide drugs are not only exposed to proteolytic enzymes and neutralizing antibodies, but are also prone to removal from the circulation by receptor-mediated cellular uptake. These events are associated with a reduction in the half-life and circulation time of the applied proteins, thereby limiting their therapeutic effectiveness. Modification of the polypeptide drugs with polymers such as PEG has been shown to protect them from enzymatic degradation and clearance to a significant extent thereby improving their pharmacodynamic and pharmacokinetic profiles. In addition, PEGylation can lead to decreased immunogenicity, increased physical and thermal stability, increased solubility, increased liquid stability, and reduced aggregation.

PEGylation is usually achieved by the covalent attachment of one or more PEG chains per monomer to a polypeptide drug. Stable linkage of PEG to proteins has the disadvantage of decreasing the protein's biological function in an irreversible manner. This can be circumvented by modifying the proteins with a reversibly-linked PEG, which has the potential to dissociate from the protein over time. This type of releasable PEG should allow liberation of the native protein, accompanied with a full regain of the native protein's activity.

SUMMARY OF THE INVENTION

The invention addresses one or more needs in the art relating to the development of in vitro assay systems to force the release of a water-soluble polymer, such as polyethylene glycol (PEG) and polysialic acid (PSA), from proteins modified with a reversibly-linked water-soluble polymer. The invention includes methods for analyzing the release of the water-soluble polymer and measuring regained protein activity. The invention further includes methods appropriate for the quality control of proteins modified with releasable water-soluble polymers.

In one embodiment, the invention includes methods of releasing a reversibly-linked water-soluble polymer from a protein modified by the water-soluble polymer. In another embodiment, the invention includes methods of increasing activity of a protein modified by a reversibly-linked water-soluble polymer. Both methods comprise the step of incubating the protein under one or more conditions effective to release the water-soluble polymer. Thus, the invention includes a combination of conditions effective to release the water-soluble polymer. In one aspect, the condition effective to release the water-soluble polymer comprises increasing pH of a buffer comprising the protein from about pH 6 to about pH 10. In another aspect, the condition comprises increasing pH of the buffer from about pH 6.1 to about pH 9.8. In a further aspect, the condition comprises increasing pH of the buffer from about pH 7.3 to about pH 9.8. In yet another aspect, the condition comprises increasing pH of the buffer from about pH 6.5 to about pH 8.1.

In another aspect, the condition effective to release reversibly-linked water-soluble polymer from a protein modified by the polymer (i.e., polyethylene glycol) comprises increasing free amine concentration of the buffer comprising the polymer-protein conjugate. In one aspect, the increased free amine concentration of the buffer is the result of an increase in the concentration of lysine. In another aspect, the increased free amine concentration of the buffer is the result of an increase in the concentration of histidine. In a further aspect, the increased free amine concentration of the buffer is the result of an increase in a combination of amines. In yet another aspect, the combination of amines is lysine and histidine.

In a further aspect, the condition effective to release reversibly-linked water-soluble polymer from a protein modified by the polymer (i.e., polyethylene glycol) comprises increasing the temperature of the buffer comprising the polymer-protein conjugate from about room temperature to about 37° C. In a further aspect, the condition effective to release the reversibly-linked water-soluble polymer from the protein comprises increasing the temperature of the buffer from about 4° C. to about 37° C.

In yet a further aspect, the condition effective to release reversibly-linked water-soluble polymer, such as polyethylene glycol, comprises extending the time period for incubating the polymer-protein conjugate from about 5 minutes to about 168 hours. In various aspects, the incubation time period extends from minutes to hours to days to even one week or more. In another aspect, the incubation time period ranges from about 5 minutes to about 48 hours.

In another embodiment, the invention includes methods of assaying quality control of proteins modified with reversibly-linked releasable water-soluble polymer comprising the steps of incubating the proteins from about 0 hours to about 6 hours at 37° C. in a buffer of about pH 7.3 comprising about 100 mM histidine and about 100 mM lysine, and analyzing protein activity within the first 6 hours. These methods, for example, provide a means for demonstrating batch-to-batch consistency or stability upon storage.

In yet another embodiment, the invention includes methods of monitoring an increase or regain of activity of a protein modified by reversibly-linked water-soluble polymer. Such methods comprise measuring protein activity before and after removing reversibly-linked water-soluble polymer from the protein.

In still another embodiment, the invention includes methods of measuring kinetics of polymer release from a protein modified by a reversibly-linked water-soluble polymer. Such methods comprise simultaneously measuring over a period of time in a reaction mixture an amount of free water-soluble polymer and an amount of reversibly-linked water-soluble polymer conjugated to a protein, wherein kinetics are determined from a change in the amount of free water-soluble polymer and a change in the amount of the polymer conjugated to the protein. In one aspect, the measuring is based on a fluorescence emission spectra, and simultaneous measuring is carried out using fluorescence at an emission peak of about 350-355 nm for polyethylene glycol -9H-(f)luoren-9-yl(m)eth(o)xy(c)arbonyl conjugates and at an emission peak of about 460-560 nm for polyethylene glycol-dibenzofulvene. In another aspect, measuring is based on high-performance liquid chromatography for free polyethylene glycol-9H-(f)luoren-9-yl(m)eth(o)xy(c)arbonyl and polyethylene glycol-dibenzofulvene. In a further aspect, measuring is immunochemically based on an enzyme-linked immunosorbent assay for polymer conjugated protein, i.e., PEGylated protein, and for free protein.

In various aspects, the water-soluble polymer includes, but is not limited to, poly(alkylene glycols) such as polyethylene glycol (PEG), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly($\alpha$-hydroxy acid), poly(vinyl alcohol), polyphosphasphazene, polyoxazoline, poly(N-acryloylmorpholine), poly(alkylene oxide) polymers, poly(maleic acid), poly(DL-alanine), polysaccharides, such as carboxymethylcellulose, dextran, hyaluronic acid and chitin, poly(meth)acrylates, as well as polysialic acid (PSA), hydroxyethyl starch, and combinations of any of the foregoing. In one aspect, the water-soluble polymer is PEG. In another aspect, the water-soluble polymer is polysialic acid (PSA).

In various aspects, the protein is factor VIII (FVIII) or von Willebrand Factor (VWF). In a further aspect of the invention, the water-soluble polymer is linked to the protein N-hydroxysuccinimide (NHS) or aldehyde-based chemistry, variants with a different chemical linkage between the water-soluble polymer chain and conjugation site, and variants differing in lengths. In one aspect, the water-soluble polymer is linked with 9H-(f)luoren-9-yl(m)eth(o)xy(c)arbonyl, dibenzofulvene, or a derivative thereof.

Other features and advantages of the invention will become apparent from the following detailed description. It should be understood, however, that the detailed description and the specific examples, while indicating specific embodiments of the invention, are given by way of illustration only, because various changes and modifications within the spirit and scope of the invention will become apparent to those skilled in the art from this detailed description.

BRIEF DESCRIPTION OF THE DRAWING

A further illustration of the invention is given with reference to the accompanying drawings, which are set out below in FIGS. 1-11.

DETAILED DESCRIPTION OF THE INVENTION

Figure 1:
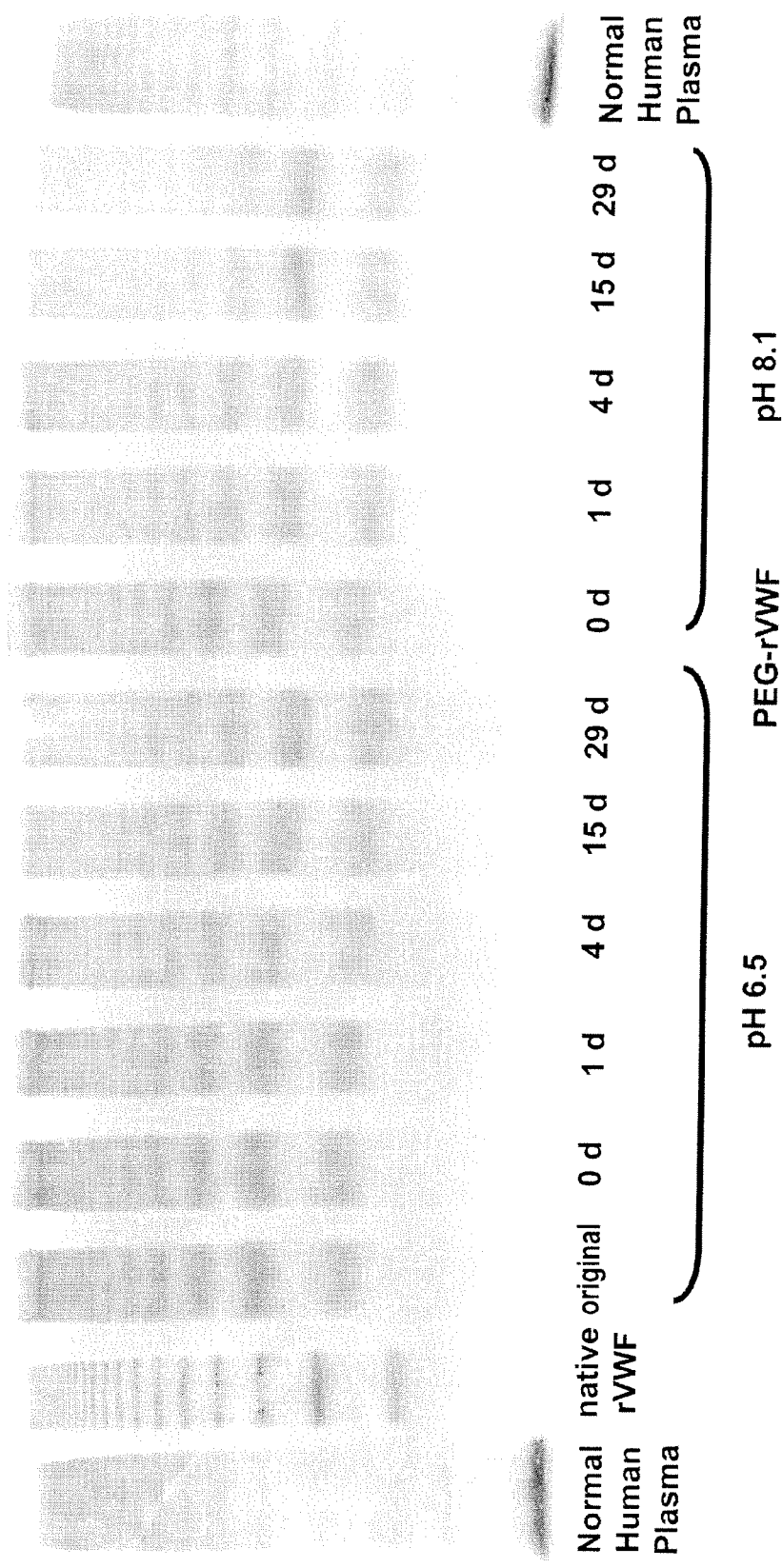
FIG. 1 shows the influence of pH-dependent PEG release on the multimeric structure of PEGylated rVWF.

The invention relates to the development of in vitro assay systems to investigate the rate of regaining activity of a protein related to the release of a water-soluble polymer, which is covalently bound to the protein via a reversible linkage. The term "regaining activity" of a protein refers to an increase in protein activity including, but not limited to, such activities as biological function, receptor binding, and enzyme activity after the water-soluble polymer is released. This type of water-soluble polymer modification of a protein is achieved by the attachment of a releasable water-soluble polymer, i.e. PEG-FMOC-NHS reagent, to exposed lysine residues of the protein of interest. The term “FMOC” stands for 9H-(f)luoren-9-yl(m)eth(o)xy(c)arbonyl which describes the protecting group on a peptide or polypeptide chain.

The term “protein” refers to any protein, protein complex or polypeptide, including recombinant proteins, protein complexes and polypeptides composed of amino acid residues linked via peptide bonds. Proteins are obtained by isolation from in vivo sources (i.e., naturally-occurring), by synthetic methods, or by recombinant DNA technology. Synthetic polypeptides are synthesized, for example, using an automated polypeptide synthesizer. A recombinant protein used according to the invention is produced by any method known in the art as described herein below. In one embodiment, the protein is a physiologically active protein, including a therapeutic protein or a biologically active derivative thereof. The term “protein” typically refers to large polypeptides. The term “peptide” typically refers to short polypeptides. Regardless of the distinction, as used herein, polypeptide, protein and peptide are used interchangeably.

A "fragment" of a polypeptide refers to any portion of the polypeptide smaller than the full-length polypeptide or protein expression product. Fragments are, in one aspect, deletion analogs of the full-length polypeptide wherein one or more amino acid residues have been removed from the amino terminus and/or the carboxy terminus of the full-length polypeptide. Accordingly, "fragments" are a subset of deletion analogs described below.

An "analogue," "analog" or "derivative" is a compound substantially similar in structure and having the same biological activity, albeit in certain instances to a differing degree, to a naturally-occurring molecule. For example, a polypeptide analog refers to a polypeptide sharing substantially similar structure and having the same biological activity as a reference polypeptide. Analogs differ in the composition of their amino acid sequences compared to the naturally-occurring polypeptide from which the analog is derived, based on one or more mutations involving (i) deletion of one or more amino acid residues at one or more termini of the polypeptide and/or one or more internal regions of the naturally-occurring polypeptide sequence, (ii) insertion or addition of one or more amino acids at one or more termini (typically an "addition" analog) of the polypeptide and/or one or more internal regions (typically an "insertion" analog) of the naturally-occurring polypeptide sequence or (iii) substitution of one or more amino acids for other amino acids in the naturally-occurring polypeptide sequence.

In one embodiment, the invention includes compositions or pharmaceutical compositions made by admixing a compound or conjugate of the invention and a pharmaceutically acceptable carrier. The term "pharmaceutical composition" refers to a composition suitable for pharmaceutical use in subject animal, including humans and mammals. A pharmaceutical composition comprises a pharmacologically effective amount of a polymer-polypeptide conjugate and also comprises a pharmaceutically acceptable carrier. A pharmaceutical composition encompasses a composition comprising the active ingredient(s), and the inert ingredient(s) that make up the pharmaceutically acceptable carrier, as well as any product which results, directly or indirectly, from combination, complexation or aggregation of any two or more of the ingredients.

The term "pharmaceutically acceptable carrier" includes any and all clinically useful solvents, dispersion media, coatings, antibacterial and antifungal agents, isotonic and absorption delaying agents, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 19th Ed. (Mack Publishing Co., Easton, 1995). Pharmaceutical carriers useful for the composition depend upon the intended mode of administration of the active agent. Typical modes of administration include, but are not limited to, enteral (e.g., oral) or parenteral (e.g., subcutaneous, intramuscular, intravenous or intraperitoneal injection; or topical, transdermal, or transmucosal administration). A "pharmaceutically acceptable salt" is a salt that can be formulated into a compound or conjugate for pharmaceutical use including, e.g., metal salts (sodium, potassium, magnesium, calcium, etc.) and salts of ammonia or organic amines.

The term "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained, or when administered using routes well-known in the art, as described below.

In one embodiment, the invention includes chemically modified proteins or polypeptides, which have been linked to a chemical moiety that provides advantageous effects to production, viability of the protein or polypeptide. For example, nonspecific or site-specific (e.g., N-terminal) conjugation of water-soluble polymers to polypeptides is known in the art to improve half-life by potentially reducing immunogenicity, renal clearance, and/or improving protease resistance. In some embodiments, polypeptides for use in the invention comprise water-soluble polymers reversibly linked to the peptide to increase the half-life and/or stability of the molecule. In various aspects, the water-soluble polymers are linked to the peptide or polypeptide at any site which can accommodate a water-soluble polymer. In one aspect, the water-soluble polymer is linked at the N-terminus. In another aspect, the water-soluble polymer is linked at the C-terminus.

The term "water-soluble polymer" refers to polymer molecules which are substantially soluble in aqueous solution or are present in the form of a suspension and have substantially no negative impact to mammals upon administration of a protein conjugated to said polymer in a pharmaceutically effective amount and can be regarded as biocompatible. In one embodiment, physiologically acceptable molecules comprise from about 2 to about 300 repeating units. In various aspects, water-soluble polymers include, but are not limited to, poly(alkylene glycols) such as polyethylene glycol (PEG), poly(propylene glycol) ("PPG"), copolymers of ethylene glycol and propylene glycol and the like, poly(oxyethylated polyol), poly(olefinic alcohol), poly(vinylpyrrolidone), poly (hydroxyalkylmethacrylamide), poly(hydroxyalkylmethacrylate), poly(saccharides), poly($\alpha$-hydroxy acid), poly(vinyl alcohol), polyphosphasphazene, polyoxazoline, poly(N-acryloylmorpholine), poly(alkylene oxide) polymers, poly(maleic acid), poly(DL-alanine), polysaccharides, such as carboxymethylcellulose, dextran, hyaluronic acid and chitin, poly(meth)acrylates, as well as polysialic acid (PSA), hydroxyethyl starch, and combinations of any of the foregoing.

In one embodiment, the invention includes the use of water-soluble polymers that vary in type, conjugation, linkage, geometry and length. The water-soluble polymer molecule is not limited to a particular structure and, in certain aspects, is linear, branched or multi-armed, dendritic, or with degradable linkages. Moreover, the internal structure of the polymer molecule is, in still other aspects, organized in any number of different patterns and is selected from the group consisting of, without limitation, homopolymer, alternating copolymer, random copolymer, block copolymer, alternating tripolymer, random tripolymer, and block tripolymer.

In certain embodiments, polymer-protein conjugates include, but are not limited to polymer-protein conjugates linked by NHS (N-hydroxysuccinimide)- or aldehyde-based chemistry, variants with a different chemical linkage between the water-soluble polymer chain and conjugation site, and variants differing in lengths.

In one aspect, the water-soluble polymer is poly(ethylene glycol) (PEG). PEG, also known as poly(ethylene oxide) (PEO) or polyoxyethylene (POE), is a type of polyether. PEG, PEO, or POE refers to an oligomer or polymer of ethylene oxide. The three names are chemically synonymous, but historically PEG has tended to refer to oligomers and polymers with a molecular mass below 20,000 g/mol, PEO to polymers with a molecular mass above 20,000 g/mol, and POE to a polymer of any molecular mass. However, herein, the terms are used interchangeably.

PEGs and PEOs include molecules with a distribution of molecular weights, i.e., polydisperse. The size distribution can be characterized statistically by its weight average molecular weight (Mw) and its number average molecular weight (Mn), the ratio of which is called the polydispersity index (Mw/Mn). Mw and Mn can be measured by mass spectroscopy. Most of the PEG-protein conjugates, particularly those conjugated to PEG larger than 1 KDa, exhibit a range of molecular weights due to a polydisperse nature of the parent PEG molecule. For example, in case of mPEG2K (Sunbright ME-020HS, NOF), actual molecular masses are distributed over a range of 1.5~3.0 KDa with a polydispersity index of 1.036. Exceptions are proteins conjugated to MS(PEG)n (N=4, 8, 12 or 24, e.g., $PEO_4$, $PEO_{12}$)-based reagents (Pierce), which are specially prepared as monodisperse mixtures with discrete chain length and defined molecular weight.

In one embodiment, when the water-soluble polymer is PEG, the average molecular weight of the PEG will range from about 3 to 200 kiloDalton ("kDa"), from about 5 kDa to about 120 kDa, from about 10 kDa to about 100 kDa, from about 20 kDa to about 50 kDa, from about 10 kDa to about 25 kDa, from about 5 kDa to about 50 kDa, or from about 5 kDa to about 10 kDa.

The term "PEG" is meant to encompass any of the forms of PEG that are discussed herein or have been used in the art to derivatize a protein. The invention includes several different linear PEG polymer lengths including but not limited to 1-100 repeating units (—CH2-CH2-O—) or conjugates of two-armed branched PEG polymers. In some aspects, PEG polymer lengths include 10-2000 repeating units (—CH2-CH2-O—) or conjugates of two-armed branched PEG polymers. Further included in the invention is NHS- or aldehyde-based PEG- $(CH_2CH_2O)_n$, having from 12 to 50 units. In general, for the PEGylation reactions included herein, the average molecular weight of the PEG moiety added is about 1 kDa to about 50 kDa (the term "about" indicating +/−1 kDa). In other aspects, the average molecular weight of the PEG moiety can be as great as about 60 kDa. In certain aspects, the average molecular weight is about 0.5-5 kDa.

The term "PEGylated" refers to a protein, protein complex or polypeptide bound to one or more PEG moieties. The term "PEGylation" as used herein refers to the process of binding one or more PEGs to a protein.

In another embodiment, the invention includes PEG-protein conjugates selected from the group consisting of linear PEG-protein conjugates that are NHS-conjugated and range in length from —(CH2-CH2-O)n-, where n=1 to 100, linear PEG-protein conjugates that are aldehyde-conjugated and range in length from —(CH2-CH2-O)n-, where n=1 to 100, two-arm branched PEG-protein conjugates that are NHS-conjugated and range in length, and three-arm branched PEG-protein conjugates that are NHS-conjugated. In other aspects, n=10 to 1000. The invention also includes PEG-protein conjugates that contain different chemical linkages (—CO $(CH_2)_n$—, and —$(CH_2)_n$— where n=1 to 5) between its conjugation site and the PEG chain. The invention further includes charged, anionic PEG-protein conjugates to reduce renal clearance, including but not limited to carboxylated, sulfated and phosphorylated compounds (anionic) (Caliceti, Adv. Drug Deliv. Rev. 2003 55(10):1261-77; Perlman, J. Clin. Endo. Metab. 2003 88(7):3227-35; Pitkin, Antimicrob. Ag. Chemo. 1986 29(3): 440-44; Vehaskari, Kidney Intl. 1982 22 127-135). In a further embodiment, the peptide is optionally conjugated to a moiety including a bisphosphonate, carbohydrates, fatty acids, or further amino acids.

In one embodiment, the invention provides modified proteins, such as blood factors having a low degree of water-soluble polymer conjugated to the protein. In various aspects of the invention, a low-PEGylated form of the protein is generated using a decreased molar excess of water-soluble polymer to protein in the conjugation reaction. For example, typical methods to PEGylate a protein use a 61.8 M excess of PEG to protein of interest. In some aspects, methods of PEGylating a protein use from 50-100 M excess of PEG to protein. In various aspects, low PEGylated proteins, as described herein, are generated using a molar excess in the reaction that is less than used in standard techniques.

Additionally, it is contemplated that the low-PEGylated protein described herein comprises at least about one and no more than about 10 water-soluble polymer moieties per blood factor molecule or per molecule of blood coagulation protein. In one embodiment, the modified protein comprises at least about 2, 3, 4, 5, 6, 7, 8, or 9 water-soluble polymer moieties per protein molecule. In another embodiment, the modified protein comprises between about 4 and 8 water-soluble polymer moieties per protein molecule. In some embodiments, the modified protein is a blood factor. In other aspects, the modified protein is a blood coagulation protein. In related embodiments, the invention includes, but is not limited to, any blood factor, such as Factor II, Factor III, Factor V, Factor VII, Factor VIII, Factor IX, Factor X, Factor XI, Factor XII, von Willebrand Factor and fibrinogen. In one aspect, the blood factor molecule is Factor VIII. In another aspect, the blood factor molecule is VWF. In a still further aspect, the blood factor molecule is human. In one embodiment, the modified blood factor or blood coagulation protein molecule comprises at least one and less than 20 PEG moieties per molecule. In a related embodiment, the modified blood factor comprises at least 4 and less than 10 PEG moieties per blood factor molecule. In a further embodiment, the modified blood factor comprises 1, 2, 3, 4, 5, 6, 7, 8, 9, 10, 11, 12, 13, 14, 15, 16, 17, 18, 19, or 20 water-soluble polymer moieties per blood factor molecule. In a related embodiment, the modified blood factor molecule comprises between 1 and 20, between 2 and 10, or between 4 and 8 PEG moieties per blood factor molecule. In one aspect, 5 PEG moieties are attached to recombinant VWF. In another aspect, 12 PEG moieties are attached to recombinant Factor VIII (rFVIII).

To determine if the in vivo therapeutic half-life of a peptide, polypeptide (protein) would benefit from PEGylation, a variety of different PEG-protein conjugates are synthesized, characterized in vitro and in vivo for pharmacokinetics.

Methods for preparing the PEGylated protein of the invention generally comprise the steps of reacting the protein of interest with PEG under conditions whereby PEG becomes reversibly attached to the N-terminus, the C-terminus, or any other amino acid of the protein, and obtaining the reaction product(s). Because PEGylating a protein might significantly alter the intrinsic activity of the protein, different types of PEG are explored. The chemistry that can be used for PEGylation of protein includes the acylation of the primary amines of the protein using the NHS-ester of methoxy-PEG (O—[(N-Succinimidyloxycarbonyl)-methyl]-O'-methylpolyethylene glycol). Acylation with methoxy-PEG-NHS or methoxy-PEG-SPA results in an amide linkage that eliminates the charge from the original primary amine (also, Boc-PEG for C-terminus). Unlike ribosome protein synthesis, synthetic peptide synthesis proceeds from the C-terminus to the N-terminus. Therefore, Boc-PEG is one method (i.e. using tert-(B)utyl(o)xy(c)arbonyl (Boc, t-Boc) synthesis) to attach PEG to the C-terminus of the peptide (R. B. Merrifield (1963). "Solid Phase Peptide Synthesis. I. The Synthesis of a Tetrapeptide". J. Am. Chem. Soc. 85 (14): 2149-2154). Alternatively, (F)luorenyl-(m)eth(o)xy-(c)arbonyl (FMOC) chemistry (Atherton, E.; Sheppard, R. C. (1989). Solid Phase peptide synthesis: a practical approach. Oxford, England: IRL Press.) is used because it does not require the hazardous use of hydrofluoric acid to remove side-chain protecting groups. Methods for generating peptides comprising a PEG moiety are well-known in the art. See, for example, U.S. Pat. No. 5,824,784.

The term "linker" refers to a molecular fragment that links the water-soluble polymer to a biologically active molecule. The fragment typically has two functional groups that can be coupled to or activated to react with another linker or directly with the biologically active nucleophile. As an example, ω-aminoalkanoic acid such as lysine is commonly used. The invention includes releasable, degradable, or hydrolyzable linkers used for conjugation of the water-soluble polymer to the polypeptide.

In one aspect, the invention includes PEG releasably linked to a protein. This type of PEG modification is achieved by the attachment of a releasable PEG-FMOC-NHS reagent to exposed lysine residues of the protein of interest. The formed conjugate is characterized by its ability to release PEG through a β-elimination mechanism. The β-elimination rate is catalyzed by bases (e.g. amine groups) and accelerated by a basic pH and increased temperature. The release of PEG can therefore be forced in vitro by high concentrations of free amines as well as by an increased pH and temperature.

In various other aspects, the invention includes stable and hydrolyzable linkers that can facilitate conjugation of the water-soluble polymer to the polypeptide of interest. Stable linkers include, but are not limited to, amide, amine, ether, carbamate, thiourea, urea, thiocarbamate, thiocarbonate, thioether, thioester, and dithiocarbamate linkages, such as ω,ω-aminoalkane, N-carboxyalkylmaleimide, or aminoalkanoic acids, maleimidobenzoyl sulfosuccinimide ester, glutaraldehyde, or succinic anhydride, N-carboxymethylmaleimide N,N'-disuccinimidyl oxalate and 1,1'-bis[6-(trifluoromethy)benzo-triazolyl]oxalate. In other aspects, the water-soluble polymer is conjugated to the polypeptide using hydrolyzable linkers. A hydrolyzable linker links a water-soluble polymer to a polypeptide by a hydrolyzable or degradable bond, which is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. In particular aspects, hydrolyzable linker systems are used. In other aspects, other degradable or releasable systems can be cleaved under special conditions, e.g. by base catalysis. Methods of making water-soluble polymers comprising hydrolyzable, degradable or releasable linkers and methods of making conjugates comprising water-soluble polymers hydrolyzable when comprising these linkers are described in U.S. Pat. No. 7,259,224 (Nektar Therapeutics) and U.S. Pat. No. 7,267,941 (Nektar Therapeutics and National Institutes of Health), U.S. Pat. No. 6,515,100 (Shearwater Corporation), WO 2006/138572 (Nektar Therapeutics), US 2008/0234193 (Nektar Therapeutics and Baxter Healthcare), WO 2004/089280 (Yeda Research and Development Co. LTD), U.S. Pat. No. 7,122,189 (Enzon Inc.), and linker systems are further described by Greenwald et al. (J. Med. Chem. 42:3657-3667, 1999). For example, a PEG can be prepared having ester linkages in the polymer backbone that are subject to hydrolysis. This hydrolysis results in cleavage of the polymer into fragments of lower molecular weight. Appropriate hydrolytically unstable or weak linkages include but are not limited to carboxylate ester, phosphate ester, anhydrides, acetals, ketals, acyloxyalkyl ether, imines, orthoesters, peptides and oligonucleotides, thioesters, thiolesters, and carbonates. Hydrolytically degradable linkages that may be contained within the polymer backbone include carbamate, carbonate, sulfate, and acyloxyalkyl ether linkages; imine linkages, resulting, for example, from reaction of an amine and an aldehyde (see, e.g., Ouchi et al., Polymer Preprints, 38(1):582-3 (1997)); carbamate, phosphate ester, hydrazone, acetal, ketal, or orthoester linkages, including acetone-bis-(N-maleimidoethyl)ketal linkers (MK). Other degradable and releasable systems included in the invention are based on FMOC chemistry or are releasable linker systems which are based on Bicin derivatives. In other aspects, other releasable systems employ 1,4- or 1,6-benzyl elimination reactions. In some aspects, the methods of the invention provide for a substantially homogenous mixture of polymer-:protein conjugate. "Substantially homogenous" as used herein means that only polymer-protein conjugate molecules are observed. The polymer-protein conjugate has biological activity and the "substantially homogenous" PEGylated protein preparations are those which are homogenous enough to display the advantages of a homogenous preparation, e.g., ease in clinical application in predictability of lot to lot pharmacokinetics.

The formed conjugate is characterized by its ability to release PEG through a β-elimination mechanism. The β-elimination rate is catalyzed by bases (e.g., amine groups) and accelerated by a basic pH and increased temperature. The release of PEG can therefore be forced in vitro by high concentrations of free amines as well as by an increased pH and temperature.

The invention describes different strategies to force the in vitro release of PEG from proteins modified by reversibly-linked PEG, as well as the development of appropriate in vitro assay systems to monitor the de-PEGylation. For example, protein conjugates, PEGylated recombinant von Willebrand Factor (rVWF) and recombinant factor VIII (rFVIII), are used.

In various embodiments, PEGylated rVWF or PEGylated rFVIII is used in the methods of the invention. PEGylated rVWF and PEGylated rFVIII are used in the treatment of various blood clotting disorders or bleeding disorders. The term "blood clotting disorder" or "bleeding disorder" refers to any of several inherited or developed deficiencies in blood clotting factors which lead to the inability of blood to efficiently form clots, and subsequent aberrant bleeding in a subject. Blood clotting disorders include, but are not limited to, hemophilia A, hemophilia B, von Willebrand syndrome, Factor X deficiency, Factor VII deficiency, Alexander's disease, Rosenthal syndrome (Factor XI deficiency or hemophilia C) and Factor XIII deficiency. Treatment of a blood clotting disorder refers to prophylactic treatment or therapeutic treatment.

Furthermore, a VWF deficiency may cause a phenotypic hemophilia A because VWF is an essential component of functional FVIII. In addition, patients suffering from von Willebrand disease (VWD) or VWF syndrome frequently exhibit an FVIII deficiency. In these patients, the reduced FVIII activity is not the consequence of a defect of the X chromosomal gene, but an indirect consequence of the quantitative and qualitative change of VWF in plasma. The differentiation between hemophilia A and VWD may normally be effected by measuring the VWF antigen or by determining the ristocetin-cofactor activity. Ristocetin cofactor activity is measured by adding ristocetin and a platelet substrate to the patient's plasma. Ristocetin enhances binding of VWF to the platelet glycoprotein Ib receptor, resulting in agglutination. The patient's VWF will support the platelet agglutination induced by the ristocetin as measured by a change in light transmission. Therefore, this is an in vitro measurement of the functional activity of the patient's VWF, and is the most sensitive assay for diagnosing VWD. Both the VWF antigen content and the ristocetin cofactor activity are lowered in most VWD patients, whereas they are normal in hemophilia A patients. The invention discusses methods involving reversibly PEGylated VWF and FVIII but includes, however, all other proteins which can be covalently bound to PEG via a reversible linkage. In various aspects, the invention included methods of releasing PEG from other blood clotting factor proteins including, but not limited to, Factor II (thrombin), Factor III, Factor V, Factor VII (proconvertin), Factor VIIa, Factor VIII, Factor IX (FIX, Christmas Factor), Factor XI, and Factor XIII subunit A and subunit B.

The release of PEG from proteins is determined by measuring an increase in free PEG, regain of protein activity, and, in the case of rVWF, for example, also, by the in vivo regain of its pharmacokinetic parameters. Monitoring possibilities of distinct PEG species without the requirement for separation are given based on the spectral properties of the condensed ring structure of the substituted fluorene (as present in the PEG-conjugate) and dibenzofulvene (free PEG) chromophors, harboring different UV absorption and fluorescence emission spectra.

One embodiment of the invention is the development of an assay system that allows monitoring of the in vitro regain of biological activity of the modified protein. Releasable water-soluble polymer, such as PEG, can be detached from the protein by increasing the pH, including, but not limited to, increasing pH to values of about 8.1, about 9.5, and about 9.8. This type of assay to regain the native protein is appropriate for proteins which are stable at high pH. In various aspects of the methods provided, pH is increased from about 6.0 to about 8.5, from about 6.5 to about 8.1, from about 6.5 to about 9.5, from about 7.3 to about 9.8, and from about 6.5 to about 9.8. In further aspects, the invention includes increasing pH to about 10. In still further aspects, the methods provided include increasing and testing pH values to about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, about 10.1, about 10.2, about 10.3, about 10.4, about 10.5, about 10.6, about 10.7, about 10.8, about 10.9, about 11.0, about 11.5 and up to greater than about pH 12.0.

In another embodiment, the addition of free amines is used as an alternative method to force the release of the water-soluble polymer at neutral pH. In some aspects, the free amines include, but are not limited to, histidine and lysine. In other aspects, cyclic amines, primary, secondary, tertiary biogenic amines, as well as aromatic amines are used. This method is therefore suitable for pH-sensitive proteins. A combination of these two approaches is also part of the invention. These approaches are illustrated with PEGylated rVWF and with PEGylated rFVIII (see Examples 1 through 5).

In another embodiment, increasing the temperature of the buffer is used as one or more additional means to force the release of the water-soluble polymer from the protein. In various aspects, the temperature is increased from about 4° C. to about room temperature to about 37° C. In still further aspects, the methods provided include increasing the temperature of the buffer from about 4° C. to about 5° C., to about 6° C., to about 7° C., to about 8° C., to about 9° C., to about 10° C., to about 11° C., to about 12° C., to about 13° C., to about 14° C., to about 15° C., to about 16° C., to about 17° C., to about 18° C., to about 19° C., to about 20° C., to about 21° C. to about 22° C., to about 23° C., to about 24° C., to about 25° C., to about 26° C., to about 27° C., to about 28° C., to about 29° C., to about 30° C., to about 31° C., to about 32° C., to about 33° C., to about 34° C., to about 35° C., to about 36° C., to about 37° C., to about 38° C., to about 39° C., to about 40° C., to about 41° C., to about 42° C., to about 43° C., to about 44° C., to about 45° C., to about 46° C., to about 47° C., to about 48° C., to about 49° C., to about 50° C., to about 55° C., to about 60° C., to about 65° C., to about 70° C., to about 75° C., to about 80° C., to about 85° C., to about 90° C., to about 95° C., and to about 100° C.

The water-soluble polymer, therefore, may be reversibly linked to a polypeptide and released from the polypeptide by increasing free amine concentration of the buffer, by increasing pH of the buffer, by increasing temperature of the buffer, or by a combination of any of the above. Moreover, in an even further embodiment, the methods of the invention include extending the time period for incubating the protein in the buffer as one or more means for releasing water-soluble polymer from the protein. In various aspects, the incubation time period is increased from about 5 minutes (min), to about 10 min, to about 20 min, to about 30 min, to about 40 min, to about 50 min, to about 1 hour (hr), to about 2 hr, to about 3 hr, to about 4 hr, to about 5 hr, to about 6 hr, to about 7 hr, to about 8 hr, to about 9 hr, to about 10 hr, to about 11 hr, to about 12 hr, to about 13 hr, to about 14 hr, to about 15 hr, to about 16 hr, to about 17 hr, to about 18 hr, to about 19 hr, to about 20 hr, to about 21 hr, to about 22 hr, to about 23 hr, to about 24 hr, to about 36 hr, to about 48 hr, to about 60 hr, to about 72 hr, to about 84 hr, to about 96 hr, to about 108 hr, to about 120 hr, to about 132 hr, to about 144 hr, to about 146 hr, to about 168 hr, to about 180 hr, to about 192 hr, to about 204 hr, to about 228 hr, to about 252 hr, to about 276 hr, and to about 300 hr. Consequently, the water-soluble polymer is in various aspects released from the polypeptide by increasing the incubation time, by increasing the amine concentration or pH of the buffer, by increasing the buffer temperature, or by a combination of one or more of any of these recited means.

In another embodiment, the invention is the development of an assay system usable for the quality control of proteins modified with releasable PEG or other releasable water-soluble polymers (see Example 6).

The invention also provides an example of a separation-based method used as a reference method for the measurement of released water-soluble polymer by size exclusion chromatography and the detection/measurement of free water-soluble polymer, i.e. PEG (see Examples 7, 8, and 9). Based on the type of water-soluble polymer linker used, the fractionation and quantification of the water-soluble polymer can be achieved by measuring the refractive index, the optical density, and/or the fluorescence of the column's effluent.

A further embodiment of the invention is the characterization of the kinetics of water-soluble polymer release by measuring the amounts of released water-soluble polymer and water-soluble polymer-protein conjugates in the reaction mixture (see Examples 7, 8, and 9), i.e. without the necessity to separate the generated species.

In one aspect, fluorescence measurements are used if the species of fluorescent molecules used differ sufficiently in their spectral properties. Simultaneous measurement of both fluorine- or dibenzofulvene-polymer and the fluorine-(FMOC)-polymer conjugated species or free water-soluble polymer (i.e. PEG) and the PEG-conjugated species is enabled by fluorescence measurements at appropriate excitation wavelengths due to differing condensed ring systems with distinct emission spectra, such as the 350-355 nm emission peak of the substituted fluorene and the 460-560 nm emission region of the dibenzofulvene. Furthermore, careful selection of the excitation wavelength also avoids excitation of the protein tryptophan and tyrosine fluorescence with a maximum sensitivity at about 280 nm. For such a measurement, a narrow spectrometer slit is preferred to separate the excitation and emission signals with a Stokes shift of about 20 nm.

In another aspect, a specific immunoassay that allows the measurement of conjugate-bound water-soluble polymer (i.e. PEG) is used. This method, as disclosed in U.S. Ser. No. 61/009,327, allows for measurement through the use of a combination of paired antibodies that specifically bind to PEG and the unconjugated protein. De-PEGylation of the PEG conjugate is then detected by a relative decrease of reactivity in the PEG protein ELISA expressed relative to the response measured for the conjugate before the De-PEGylation (see Examples 7, 8, and 9). An ELISA of this type does not detect free PEG, but specifically detects only PEG bound to conjugate.

With the development of these in vitro assay systems, it is possible to increase the β-elimination-driven rate of PEG release from reversibly PEGylated proteins in a substantial manner and to regain activity of the unmodified protein.

EXAMPLES

Additional aspects and details of the invention are apparent from the following examples, which are intended to be illustrative rather than limiting. Example 1 describes in vitro de-PEGylation of releasable PEG-rVWF at increased pH; Example 2 describes in vitro de-PEGylation of releasable PEG-rVWF in the presence of primary amines and high pH; Example 3 describes in vitro recovery of protein activity of releasable PEG-RFVIII in the presence of selected free amines; Example 4 describes in vitro de-PEGylation of releasable PEG-rFVIII in the presence of a combination of free amines; Example 5 describes in vitro de-PEGylation of releasable PEG-rFVIII in the presence of Hepes/Tris; Example 6 describes in vitro recovery of protein activity of releasable PEG-rFVIII in the presence of selected free amines; Example 7 describes the detection of PEG release from PEG-rFVIII by fluorescence measurement without separation of species; Example 8 describes the scavenging of PEG-dibenzofulvene by glutathione; Example 9 demonstrates the effect of pH on PEG-dibenzofulvene generation; Example 10 discusses in vitro de-polymerization of releasable PSA-rVWF at increased pH; Example 11 describes in vitro de-polymerization of releasable PSA-rVWF in the presence of primary amines and high pH; Example 12 describes in vitro recovery of protein activity of releasable PSA-RFVIII in the presence of selected free amines; Example 13 describes in vitro de-polymerization of releasable PSA-rFVIII in the presence of a combination of free amines; and Example 14 describes in vitro de-polymerization of releasable PSA-rFVIII in the presence of Hepes/Tris.

Example 1

In Vitro De-PEGylation of Releasable PEG-rVWF at Increased PH

De-PEGylation of a releasable PEG rVWF conjugate (conjugated with a 20K branched PEG) was carried out by incubating the protein at two different pH values, pH 6.5 and pH 8.1. Purified PEG-rVWF was dissolved in 0.02 M Na-Citrate, 0.15 M NaCl with a pH value of 6.5. For the alkaline sample, the same buffer was adjusted to pH 8.1 by the addition of 0.1 M NaOH. Sub-samples were withdrawn at defined time points and analyzed regarding their content of VWF antigen (VWF:Ag), free PEG, total PEG, and VWF composition of multimers.

The content of VWF:Ag was determined with a sandwich ELISA using commercially available antibodies (Dako, Glostrup, Denmark). Free PEG and total PEG were determined by a high-performance liquid chromatography (HPLC) method provided by Nektar Therapeutics (Huntsville, Ala.). The terms "high-performance liquid chromatography," "high pressure liquid chromatography," and HPLC are used interchangeably herein. VWF multimer analysis was performed by high-density horizontal SDS agarose gel electrophoresis and immunostaining using a polyclonal anti-human VWF antibody (Dako). The results of these experiments are summarized in Table 1 and FIG. 1.

The data in Table 1 show the results for the determined ratio of VWF:Ag to protein (IU/mg) and the percentage of released, free PEG on the total PEG content during the incubations at pH 6.5 and pH 8.1, respectively. The basis value reflects the initial properties of the conjugate, i.e. before forced PEG release has been initiated. The ratio of VWF:Ag to protein was markedly decreased for PEG-rVWF (39 IU/mg) compared to 100-160 IU/mg for a native, unmodified rVWF. The percentage of free PEG was as low as 5%. Upon incubation at 37° C. the VWF:Ag to protein ratio gradually increased over time under both conditions, but with slightly higher values at pH 8.1. The amount of PEG released from the PEG-rVWF conjugate was significantly accelerated at higher pH. After 1 h at pH 8.1, the percentage of released, free PEG was 53%; whereas at the lower pH 6.5, 23% of free PEG had been liberated. The difference seen in the percentage of released PEG diminished upon longer incubation times and after 29 days, where 60% of the PEG was released at pH 6.5, and 68% of total PEG was liberated at pH 8.1.

TABLE 1

Changes in VWF:Ag values and appearance of free PEG upon incubation of reversibly PEGylated rVWF at elevated pH.

| | PEG-rVWF | | | |
|---|---|---|---|---|
| Incubation time | Ratio VWF:Ag/protein (IU/mg) | | Free PEG (% of total PEG) | |
| (days) | pH 6.5 | pH 8.1 | pH 6.5 | pH 8.1 |
| Basis | 39 | 39 | 5 | 5 |
| 5 min | 42 | 56 | 3 | 29 |
| 1 | 58 | 78 | 23 | 53 |
| 4 | 64 | 71 | 41 | 58 |
| 15 | 77 | 86 | 54 | 63 |
| 29 | 79 | 92 | 60 | 68 |

Multimer analysis of these samples (FIG. 1) shows the typical shift of each VWF multimer after PEGylation (when lanes designated 'native rVWF' and 'original' are compared). During incubation at both pH 6.5 and 8.1, the molecular weight of the PEGylated rVWF multimers gradually decreased, discernible by the shift back to lower molecular weights, indicating the release of PEG over time. Complete restoration of the original structure of unmodified rVWF was, however, not achieved under both pH conditions. The data nonetheless show that incubation at both pH 6.5 and pH 8.1 at 37° C. resulted in substantial release of PEG from PEGylated rVWF.

Example 2

In Vitro De-PEGylation of Releasable PEG-rVWF in the Presence of Primary Amines and High PH A releasable PEG-rVWF (20 k branched PEG) conjugate was diluted in a 0.02 M sodium citrate, 0.15 M NaCl buffer at a pH of 9.8, containing 100 mM lysine, and incubated at 37° C. Sub-samples were withdrawn at defined time points and analyzed for their content of VWF antigen (VWF:Ag), free PEG, total PEG, and multimeric composition. Multimer analysis was performed by high-density horizontal SDS agarose gel electrophoresis and immunostaining using antibodies either directed against human VWF (Dako, Glostrup, Denmark) or PEG (in-house developed polyclonal rabbit anti-PEG antibody). The results are summarized in Table 2, FIG. 2, and FIG. 3.

TABLE 2

Changes in VWF:Ag values and appearance of free PEG upon incubation of reversibly PEGylated rVWF at elevated pH and in the presence of free amines.

| Incubation time (hrs) | PEG-rVWF pH 9.8 100 mM lysine | |
|---|---|---|
| | Ratio VWF:Ag/protein (IU/mg) | Free PEG (% of total PEG) |
| Basis | 26 | 3 |
| 5 min | 33 | 5 |
| 0.5 | 53 | 33 |
| 4 | 80 | 63 |
| 10 | 87 | 75 |
| 20 | 96 | 79 |
| 48 | 105 | 81 |

Figure 2:
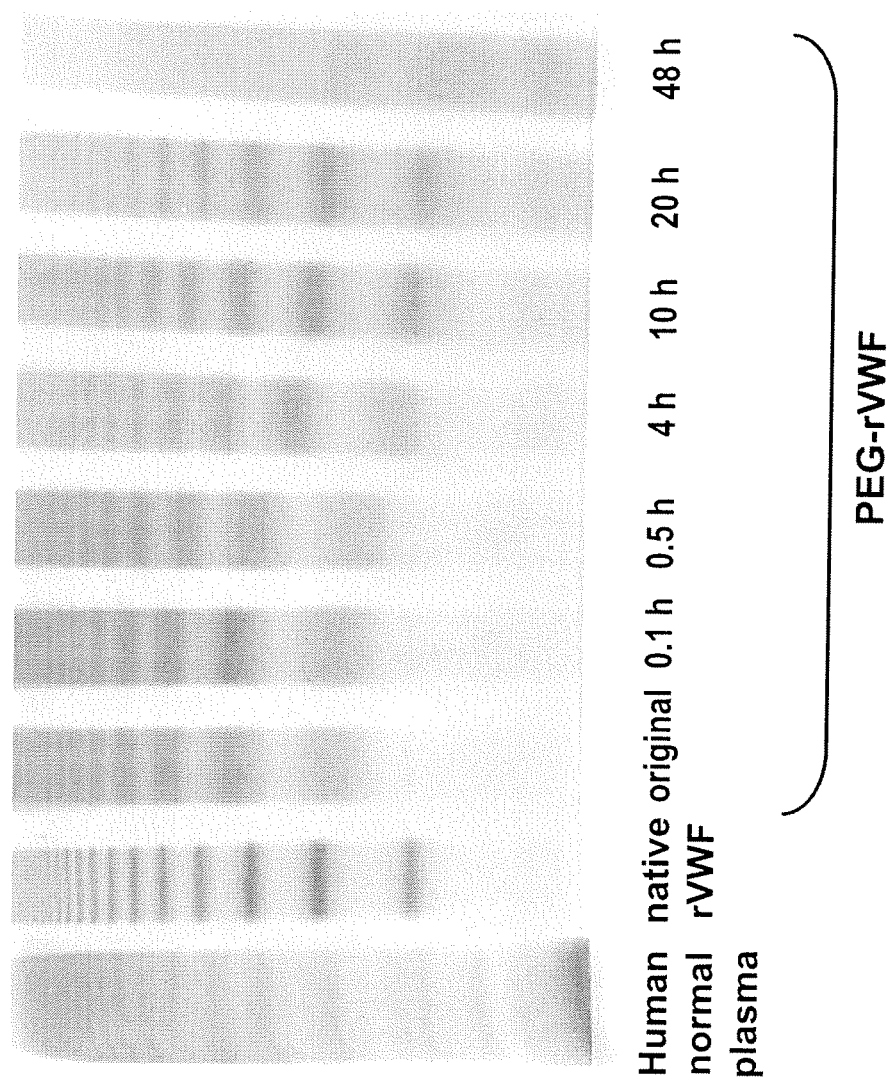
FIG. 2 shows the influence of pH- and amine-dependent PEG release on the multimeric structure of PEGylated rVWF using an anti-VWF antibody.
Figure 3:
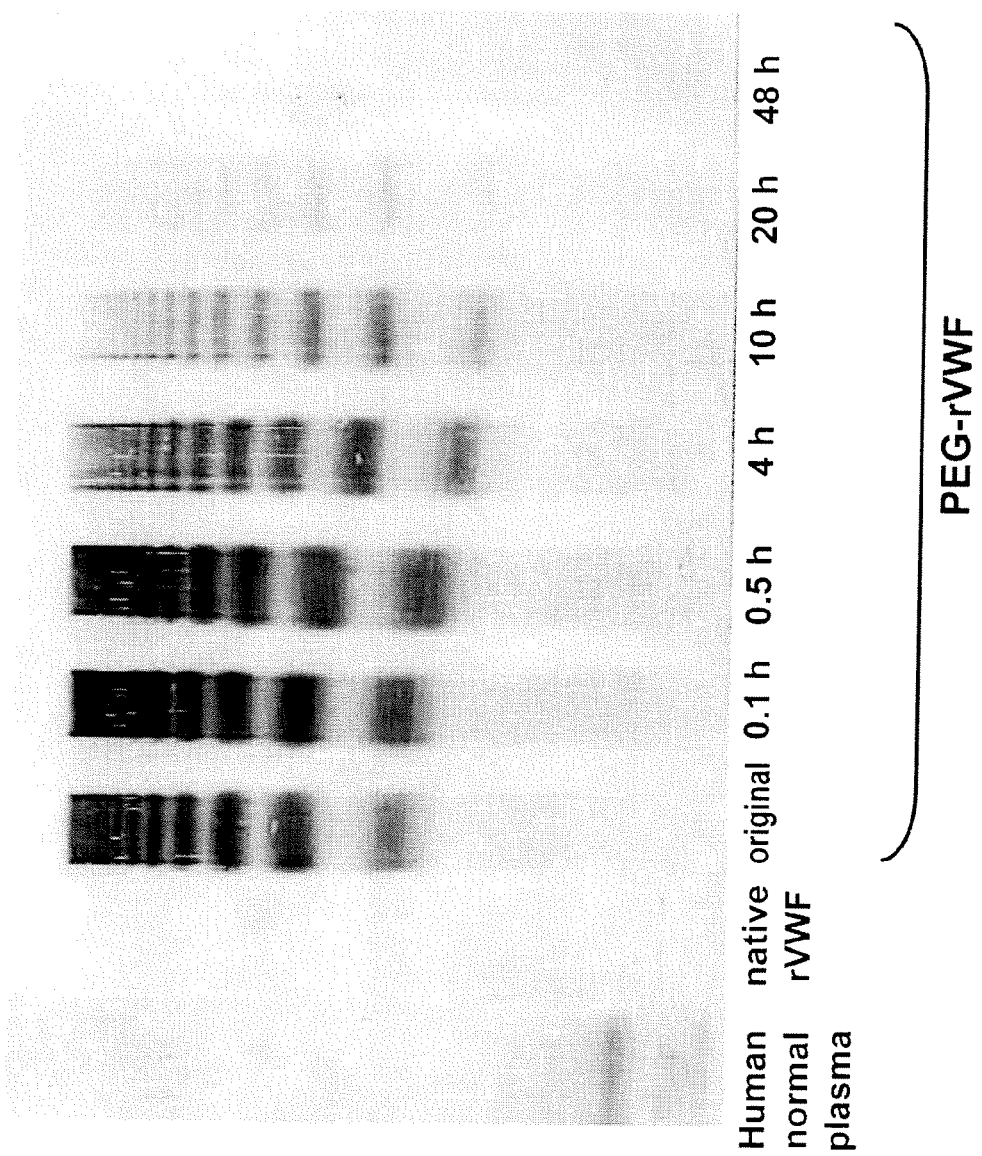
FIG. 3 shows the influence of pH- and amine-dependent PEG release on the multimeric structure of PEGylated rVWF using an anti-VWF antibody.

The data in Table 2 show that upon incubation of PEG-rVWF in the presence of the amine lysine at pH 9.8, a clear increase in the ratio of VWF:Ag to protein occurred over time. Furthermore, 81% of the total PEG was released after 48 h of incubation in the recited buffer. The multimer gel in FIG. 2 shows that after 10-20 h of incubation, the VWF multimers shifted back to lower molecular weights and the structure became similar to that of an unmodified rVWF. Longer incubation (48 h) time resulted in a degradation of the rVWF protein structure. De-PEGylation of rVWF was directly demonstrated by using a polyclonal anti-PEG antibody for the staining of the multimer gel in FIG. 3. After 20 h of incubation, only minor amounts of PEG remained bound to the single VWF multimers. The data show that incubation in the presence of lysine at pH 9.8 resulted in a clear release of PEG in a shorter time period compared to Example 1 and restored rVWF structure. The method described by Example 2 is thus suitable for proteins that are stable at high pH.

Pharmacokinetics of the de-PEGylated PEG-rVWF was determined in a VWFxFVIII double knock-out mouse model. Mice received a bolus injection (10 ml/kg) via the tail vein of FVIII (200 IU/kg), alone or together with either 1.6 mg/kg of native rVWF, releasable PEG-rVWF (20K branched) or de-PEGylated rVWF (incubated for 10 h at +37° C. in lysine solution at pH 9.8).

Figure 4:
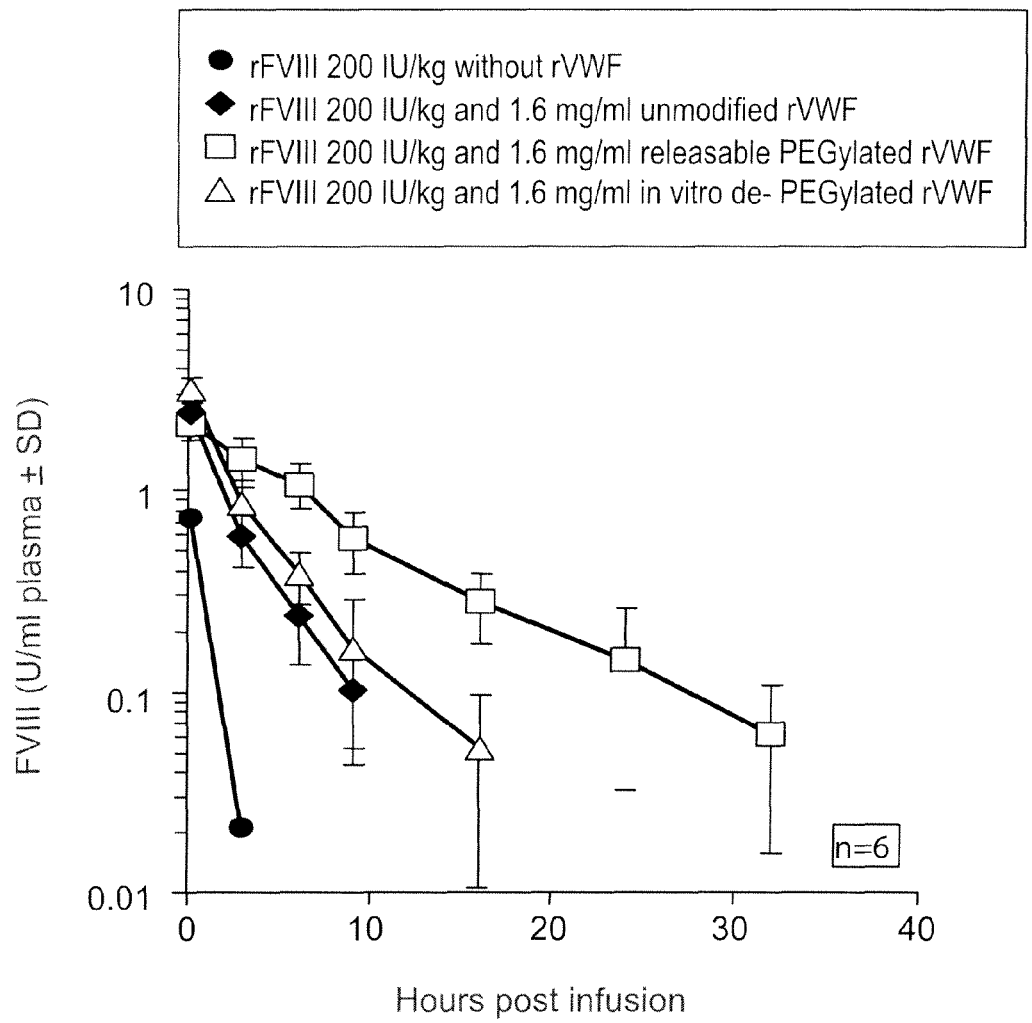
FIG. 4 shows a comparison of the in vivo rFVIII-stabilizing effect of native and de-PEGylated rVWF in a FVIII×VWF-deficient mouse model.

Blood samples (anti-coagulated with sodium citrate) were withdrawn by heart puncture after anesthesia from the respective groups after 5 min, and at 3 h, 6 h, 9 h, and 24 h after injection. Plasma was prepared by centrifugation and the in vivo FVIII-stabilizing function of VWF was determined by measuring FVIII activity with a chromogenic assay. The results of this experiment are summarized in FIG. 4, showing that the PEGylated rVWF protected FVIII to a greater extent than unmodified rVWF. The de-PEGylated-rVWF retained the same FVIII stabilizing capacity as the unmodified rVWF, indicating that active rVWF was liberated during the forced in vitro release.

Example 3

Figure 5:
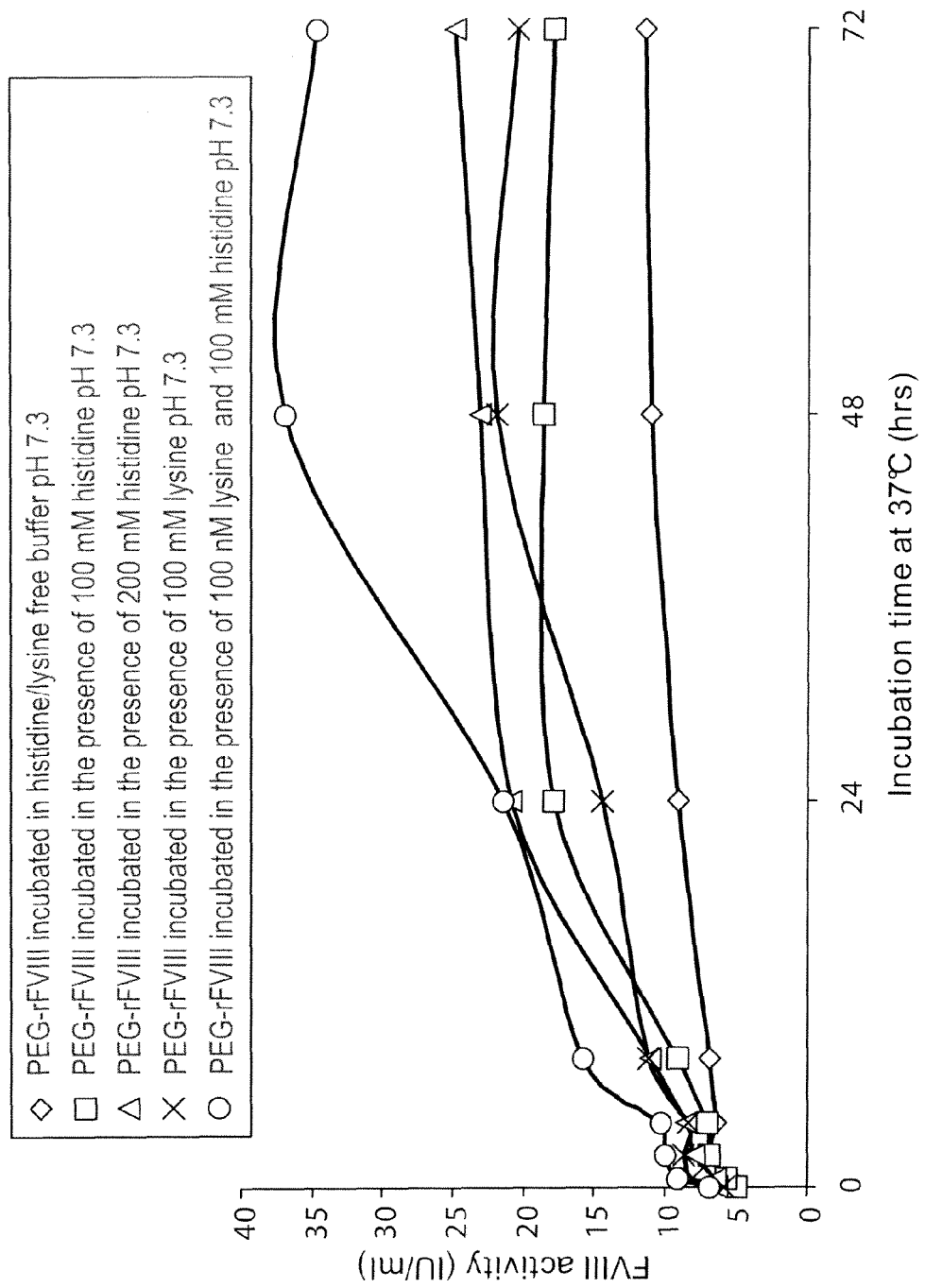
FIG. 5 shows a comparison of FVIII chromogenic activity increase upon incubation of PEG-rFVIII in buffer containing histidine and/or lysine at different concentrations.

In Vitro Recovery of Protein Activity of Releasable PEG-rFVIII in the Presence of Selected Free Amines A releasable PEG-rFVIII conjugate (20 K branched PEG) was diluted to 5 IU/ml FVIII chromogenic activity in a buffer with a pH of 7.3 (10 mM histidine, 90 mM NaCl, 1.7 mM $CaCl_2$, 10 mM Tris, 0.26 mM glutathione, 176 mM mannitol, 23.5 mM trehalose, and 0.1 g/l Tween 80); the buffer additionally contained lysine, histidine, or a combination of both amino acids, and the buffer was incubated at 37° C. to force the in vitro release of PEG from the protein conjugate. Sub-samples were withdrawn at defined time points (24 h, 48 h, and 72 h) and FVIII chromogenic activity was determined online by use of a FVIII chromogenic assay. The results are summarized in FIG. 5.

In a buffer lacking amines, activity increased from 5.0 to 11.5 IU/ml FVIII:C after 72 h. At the 72 h time point, the presence of 100 mM histidine increased FVIII activity to 17.8 IU/ml, 100 mM lysine to 20.4 IU/ml, 200 mM histidine to 24.9 IU/ml, and the combination of 100 mM histidine and 100 mM lysine to 34.7 IU/ml. Thus, the forced PEG release was clearly dependent on the amine concentration and possibly on the amine composition. The method described herein by this example is suitable for in vitro recovery of protein activity of reversibly PEGylated proteins that are sensitive to the pH environment.

Example 4

In Vitro De-PEGylation of Releasable PEG-rFVIII in the Presence of a Combination of Free Amines A releasable PEG-rFVIII conjugate (20 k branched PEG) was incubated in a buffer (20 mM $Na_3$ citrate, 1.7 mM $CaCl_2$, 176 mM mannitol, 36 mM sucrose, and 0.1 g/l Tween 80) with a pH of 7.3; the buffer additionally contained 100 mM histidine and 100 mM lysine, and was incubated at +37° C. Sub-samples were withdrawn at defined time points up to 168 h and the functional activity of PEG-rFVIII was determined online by use of the FVIII chromogenic assay. In addition, the release of PEG was confirmed by measuring free PEG and total PEG by an HPLC method provided by Nektar Therapeutics (Huntsville, Ala.) from frozen sub-samples. The results are summarized in FIG. 6, and Table 3.

Figure 6:
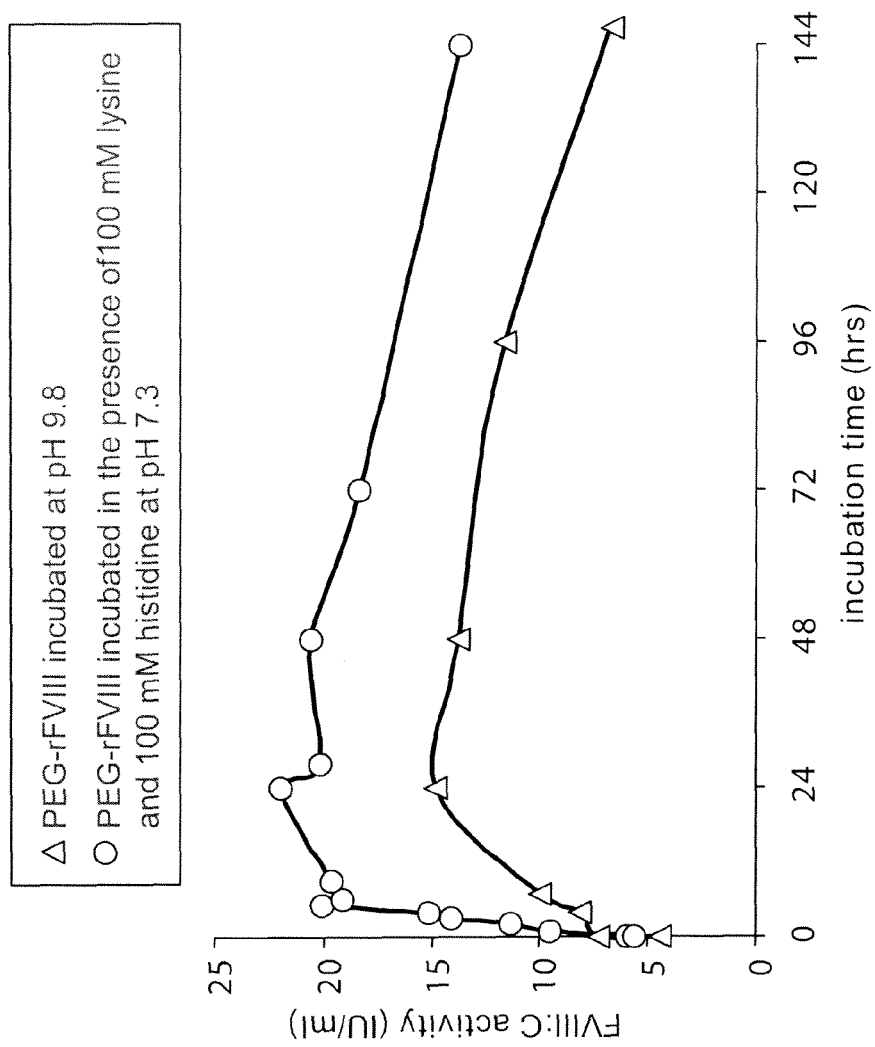
FIG. 6 shows a comparison of FVIII chromogenic activity increase upon incubation of PEG-rFVIII at pH 9.8 or in a neutral pH buffer containing histidine and lysine.

FIG. 6 shows the increase of the FVIII chromogenic activity of PEG-rFVIII during the incubation phase. The increase in protein activity followed a two-phase course: a rapid increase in FVIII activity was observed within the first 6 h followed by a phase with a slow activity increase reaching a maximum after 24 h of incubation, with an increase in FVIII chromogenic activity to 21.9 IU/ml compared to 6.0 IU/ml starting activity, which corresponds to an activity increase of 366%. Further incubation up to 144 h resulted in a slow, gradual decrease of FVIII activity. As outlined in Examples 1 and 2, the incubation of PEGylated proteins at high pH (e.g. 9.8) is another option for triggering a PEG release in vitro. The same PEG-rFVIII conjugate was therefore incubated at pH 9.8 at 37° C. and the increase in activity was compared to that achieved in the presence of histidine/lysine at pH 7.3. FIG. 6 shows that at pH 9.8, less FVIII chromogenic activity was recovered, with an increase in FVIII chromogenic activity to 14.8 IU/ml at the 24 h time point compared to 4.4 IU/ml starting activity. This was probably due to enhanced FVIII inactivation at this high pH value. This conclusion was supported by similar rates of PEG release under both conditions (Table 3). The amount of PEG released was expressed as the percentage of free PEG in relation to the total amount of PEG. The initial low content of free PEG (8 to 13%=basis values) increased upon incubation in both buffers in a time-dependent manner, reaching a maximum of 64% of the total PEG after 144 h in the case of the histidine/lysine buffer and of 74% after 168 h for the alkaline buffer (pH 9.8). These data confirm that both conditions are appropriate for triggering the release of PEG.

TABLE 3

Changes in free PEG content of PEG-rFVIII in the presence of free amines at neutral pH and at pH 9.8.

| Incubation | PEG-rFVIII free PEG (% of total PEG) | |
| --- | --- | --- |
| time (hrs) | His/Lys pH 7.3 | pH 9.8 |
| basis | 8 | 13 |
| 5 min | 18 | Nd |
| 2 | 24 | Nd |
| 10 | 37 | Nd |
| 24 | 45 | 37 |
| 48 | 51 | Nd |
| 72 | 55 | 49 |
| 96 | 59 | Nd |
| 120 | 62 | Nd |
| 144 | 64 | Nd |
| 168 | Nd | 74 |

The data in Example 6 also suggest that for pH-sensitive proteins combined free amines at neutral pH are to be favored for the forced in vitro PEG release as the recovery of protein activity is higher under such conditions compared to an alkaline-driven release.

Example 5

In Vitro De-PEGylation of Releasable PEG-rFVIII in the Presence of Hepes/Tris

Figure 7:
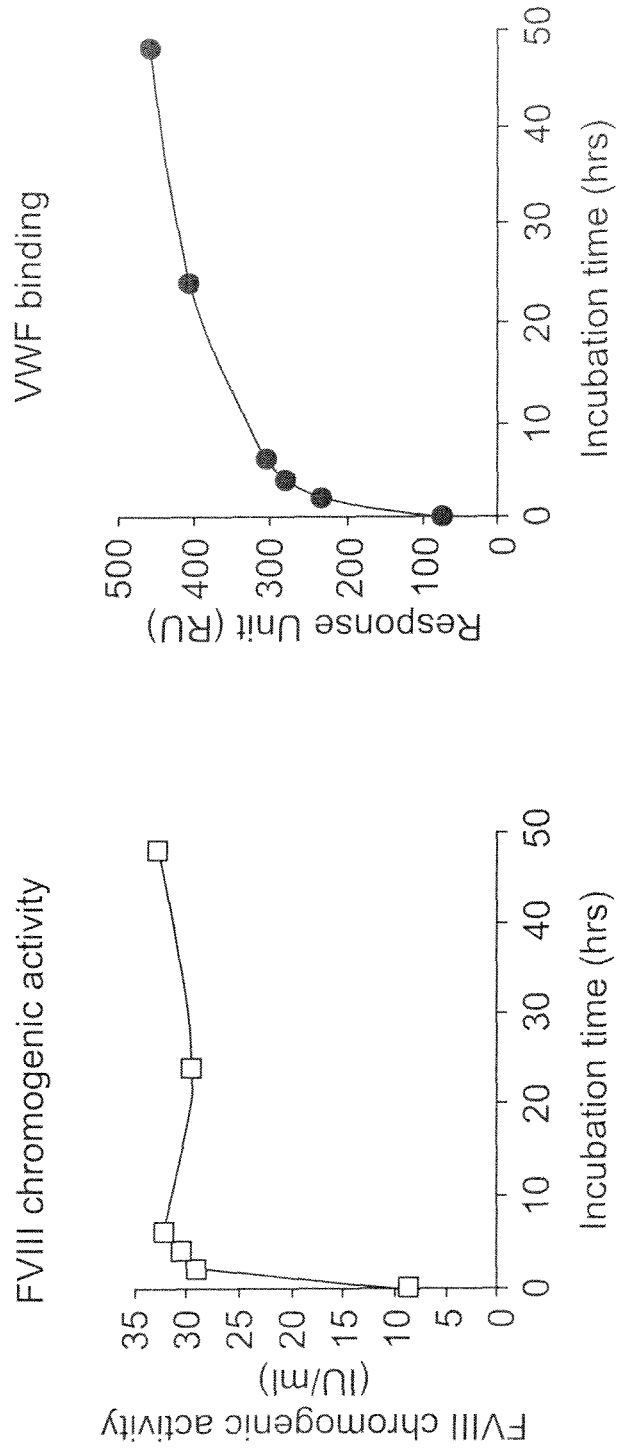
FIG. 7 shows the influence of amine-based buffer-dependent PEG release on FVIII chromogenic activity and VWF-binding ability of PEG-rFVIII.

Releasable PEG-rFVIII (20 k branched PEG) was incubated at 37° C. in a combination of typical amine-containing buffer substances at pH 7.4, namely 200 mM HEPES and 200 mM Tris. Sub-samples were withdrawn at defined time points, the recovery of FVIII activity was monitored by a chromogenic assay, and its ability to interact with VWF was determined. VWF binding, which critically determines survival of FVIII in the circulation, was monitored by using surface plasmon resonance technology. Using Biacore equipment, the various PEG-rFVIII samples were injected into the mobile phase and tested for interaction with immobilized VWF. While only low levels of PEG-rFVIII bound to the rVWF, the binding of the sample increased with PEG-release. FIG. 7 shows the increasing chromogenic FVIII activity with time that is accompanied by an increase in rFVIII binding to VWF, which is a signal of de-PEGylation. The data of Example 5 indicate that a wide spectrum of amines can be used to force the release of PEG from such conjugates. The regain of both chromogenic activity and binding to VWF further shows that functional protein is generated over time.

Example 6

Figure 8:
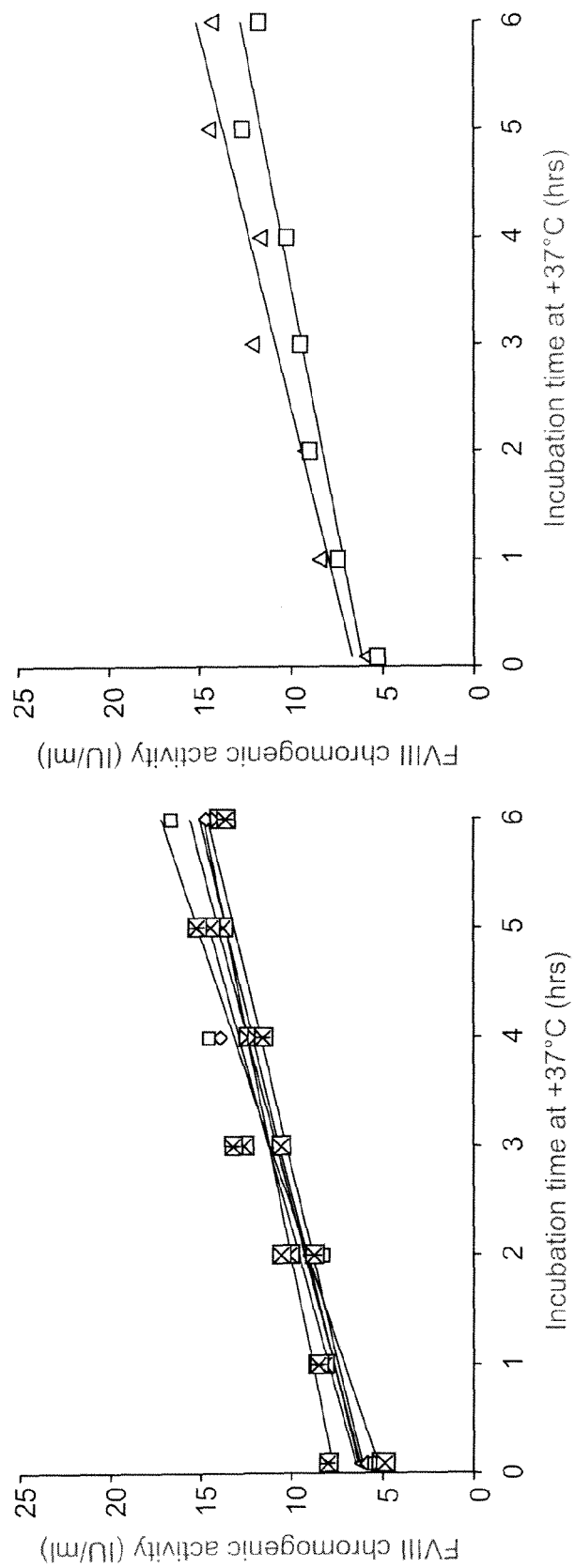
FIG. 8 shows the reproducibility of the in vitro release assay and its test for controlling batch to batch consistency.

Initial rate of FVIII Activity Increase Upon Incubation of PEG-rFVIII in the Presence of Free Amines The initial rapid phase of PEG release from PEG-rFVIII, which was defined in Example 4 as the time interval from 0 to 6 h of incubation at 37° C., was analyzed for its suitability as a parameter to investigate batch to batch consistency. FIG. 8 shows the increase in FVIII activity upon incubation in a 100 mM histidine/100 mM lysine buffer of pH 7.3 at 37° C. within the first 6 h.

In the left panel, six repeated measurements of the same PEG-rFVIII batch are displayed, whereas in the right panel, the mean activity values of two distinct batches of the conjugate are shown. The increase in FVIII activity (IU/ml) per hour is calculated by fitting the curves by linear regression and expressed as the slope (k'). The numeric values of the slope for the six test units and the two batches are summarized in Table 4. In both cases, similar slopes were obtained, thereby demonstrating that the assay system yields reproducible results. Moreover, determining the initial rate of FVIII activity increase allows a comparison of different batches of a releasable PEG conjugate.

TABLE 4

Initial rate of FVIII chromogenic activity increase in a forced-PEG release reaction.

| | Slope (k') |
| --- | --- |
| Test unit | |
| 1 | 1.48 |
| 2 | 1.58 |
| 3 | 1.42 |
| 4 | 1.65 |
| 5 | 1.19 |
| 6 | 2.01 |
| Batch | |
| 1 | 1.43 |
| 2 | 1.31 |

Example 7

Figure 9:
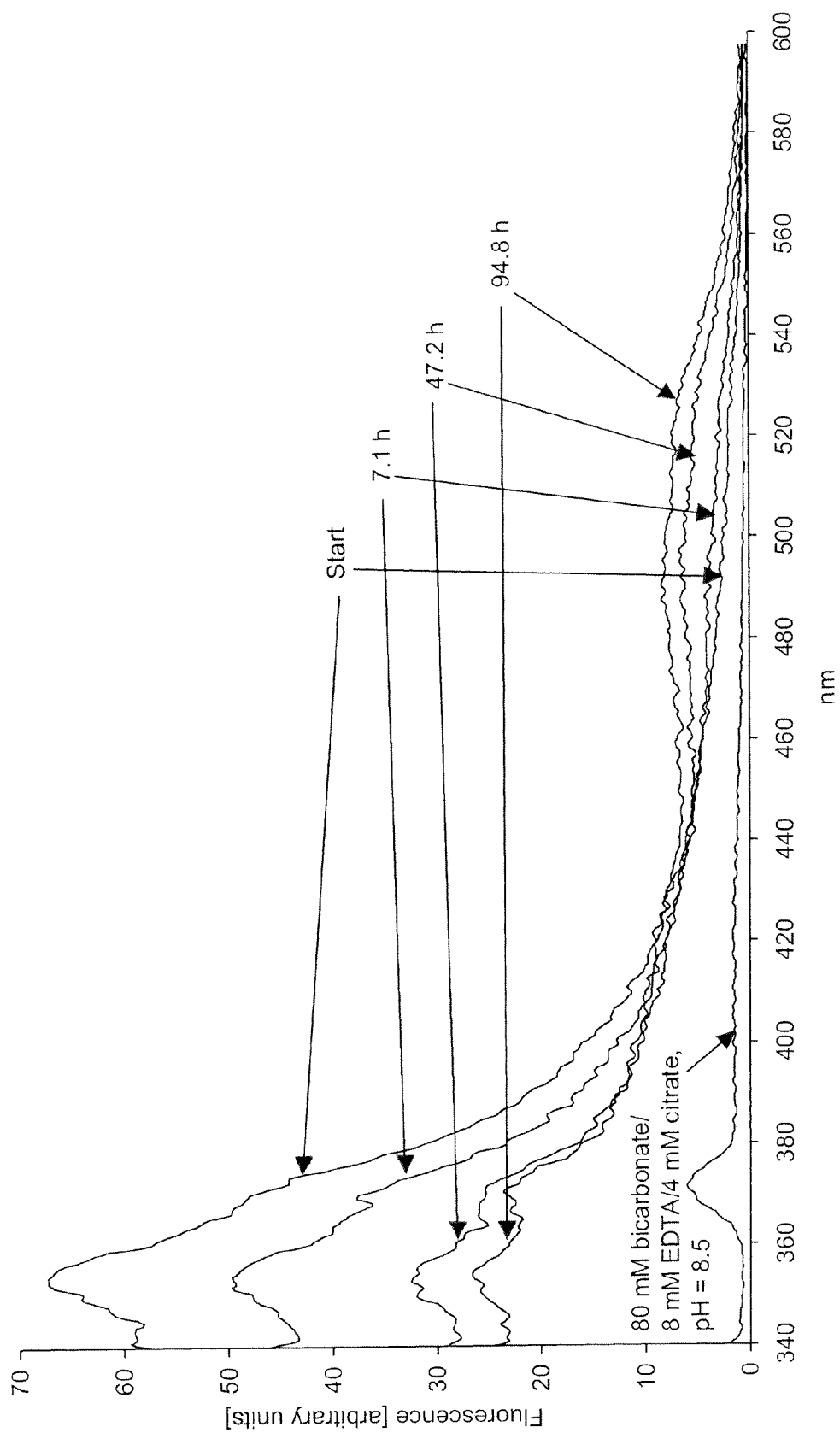
FIG. 9 shows the fluorescence spectra illustrating the generation of PEG-dibenzofulvene (460-560 nm) and the corresponding decrease of the PEG-FMOC-conjugate fluorescence signal (350-355 nm) upon incubation of PEG-rFVIII at pH=8.5.

Detection of PEG-Release from PEG-rFVIII by Fluorescence Measurement without Separation of Species Releasable PEG increased in FVIII chromogenic activity of 21.9 IU/ml compared to 6.0 IU/ml starting activity rFVIII (20 k branched PEG), formulated in 20 mM citrate buffer, pH=6.0, containing 32 g mannitol, 12 g sucrose, 2.5 g $CaCl_2.2H_2O$, and 100 mg polysorbate 80 per liter, and freeze-dried, was reconstituted to a solution containing 360 mg protein (bichinchonic acid assay) and 345 mg of total PEG. This solution was diluted 1:5 in a 100 mM sodium bicarbonate solution, pH=8.5, containing 32 g mannitol, 12 g sucrose, 2.5 g $CaCl_2.2H_2O$, 10 mM EDTA, and 100 mg polysorbate 80 per liter (99% oleic acid, Nippon Oils and Fats), and the fluorescence spectra, showing the PEG-FMOC-compounds at a narrow peak between 350-355 nm and the released PEG-dibenzofulvene (PEG-DBF) in a broad peak between 460-560 nm, measured on a Perkin Elmer LS50B spectrofluorimeter (1.25 mL in a 0.4 (excitation)×1 (emission) cm PTFE-stoppered quartz cuvette, 330 nm excitation/340-600 nm emission wavelength, 5/5 nm slit width, 180 nm/min scanning speed, 800 V photomultiplier voltage) upon incubation at 20-25° C. at defined time intervals (FIG. 9).

TABLE 5

Summary of quantitative analysis of PEG-FVIII and PEG-derivatives upon incubation of PEG-rFVIII at pH 8.5.

| PH 8.5 | FMOC-PEG HPLC | | DBF-PEG HPLC | | DBF-PEG 330 nm/E460-560 nm | | FMOC-PEG 330 nm/E350-355 nm | | PEG-FVIII ELISA | | FVIII:Ag ELISA | |
|---|---|---|---|---|---|---|---|---|---|---|---|---|
| h | µg/mL | % start | µg/mL | % start | Intensity | % start | S350-355 | % start | % ref | % start | U/mL | % start |
| 0.0 | 15.5 | 100.0 | 3.7 | 100.0 | 457 | 100.0 | 727 | 100.0 | 112.1 | 100.0 | 28.1 | 100.0 |
| 1.7 | 20.9 | 134.8 | 5.6 | 151.4 | 468 | 102.4 | 624 | 85.8 | 80.2 | 71.5 | 47.1 | 167.6 |
| 3.4 | 24.1 | 155.5 | 7.8 | 210.8 | 514 | 112.6 | 583 | 80.2 | 81.1 | 72.3 | 53.4 | 190.0 |
| 5.2 | 25.7 | 165.8 | 9.5 | 256.8 | 561 | 122.7 | 558 | 76.7 | 71.9 | 64.1 | 59 | 210.0 |
| 7.1 | 27.3 | 176.1 | 11.0 | 297.3 | 611 | 133.8 | 540 | 74.2 | 60.8 | 54.2 | 69.3 | 246.6 |
| 22.8 | 33.1 | 213.5 | 16.8 | 454.1 | 845 | 185.0 | 496 | 68.2 | 54.7 | 48.8 | 86.9 | 309.3 |
| 31.0 | 35.9 | 231.6 | 20.2 | 545.9 | 850 | 186.1 | 419 | 57.7 | 45.9 | 40.9 | 96.1 | 342.0 |
| 47.2 | 40.1 | 258.7 | 24.7 | 667.6 | 994 | 217.5 | 351 | 48.3 | 39.7 | 35.4 | 116.8 | 415.7 |
| 53.9 | 41.8 | 269.7 | 27.2 | 735.1 | 1039 | 227.5 | 325 | 44.7 | 37.1 | 33.1 | 111.9 | 398.2 |
| 71.3 | 43.7 | 281.9 | 29.6 | 800.0 | 1201 | 262.8 | 322 | 44.2 | 31.4 | 28.0 | 131.5 | 468.0 |
| 78.4 | 45.1 | 291.0 | 30.7 | 829.7 | 1182 | 258.6 | 280 | 38.5 | 28.0 | 25.0 | 146.9 | 522.8 |
| 94.8 | 54.5 | 351.6 | 38.6 | 1043.2 | 1288 | 281.9 | 286 | 39.4 | 30.1 | 26.9 | 150.6 | 535.9 |

Samples drawn at these designated intervals from a separate reservoir were analyzed by HPLC on a Shodex protein 5µ column (KW-803 300A, 300×8 mm (Showa Denko America, Inc. (New York, N.Y.)) operated with 20 mM sodium phosphate, 50 mM sodium sulfate, at pH 6.1 for free FMOC-PEG and dibenzofulvene-PEG, and were analyzed immunochemically by ELISA for PEG-FVIII and free FVIII antigen. Results of the PEG-FVIII ELISA are given as the measured binding in the assay relative to that of a freshly dissolved standard preparation. Fluorescence signals were integrated from 350-355 nm and from 460-560 nm (in 0.5 nm steps) for PEG-FMOC conjugates and PEG-dibenzofulvene, respectively. The data are summarized in Table 5.

The data presented in Table 5, shown as a percent of the initially measured concentrations, demonstrate the release of free benzofulvene-PEG, as shown by the increase in the fluorescence signal at 460-560 nm, and of free FVIII antigen, as measured by ELISA, and by the corresponding decrease of the PEG-FMOC protein conjugate, as shown by the 350-355 nm fluorescence signal and the decreased levels of FVIII-bound PEG as measured by the PEG-FVIII ELISA.

Example 8

Scavenging of PEG-Dibenzofulvene by Glutathione

Figure 10:
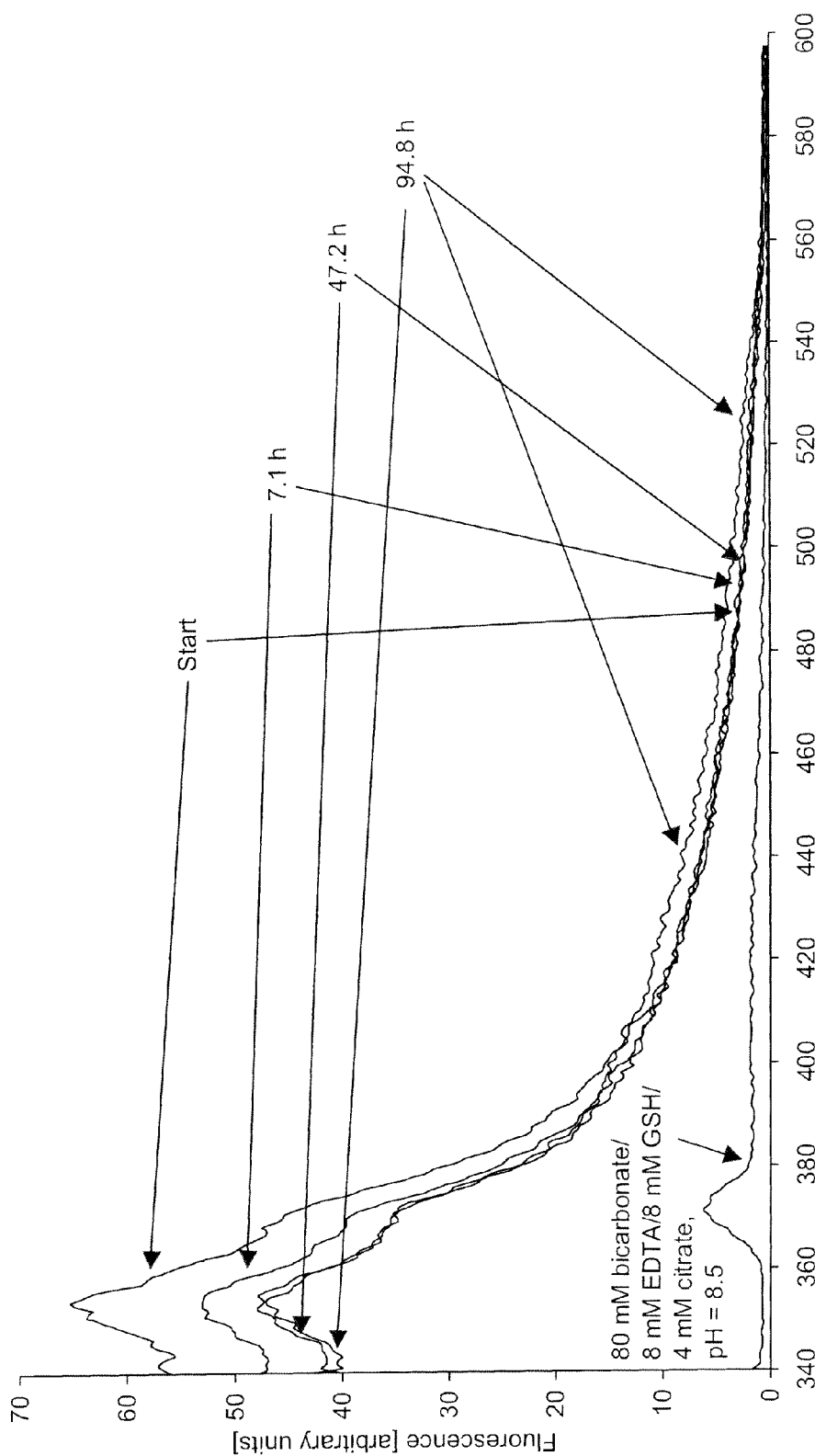
FIG. 10 shows the fluorescence spectra illustrating the slight decrease of the PEG-FMOC-conjugate fluorescence signal (350-355 nm) without the formation of PEG-dibenzofulvene fluorescence upon incubation of releasable-PEGylated FVIII at pH=8.5 in the presence of reduced glutathione.

To the bicarbonate solution of Example 7, 10 mM reduced glutathione (GSH) was added, and dilution, incubation, measurement, sampling, and analysis were carried out as set out in Example 8. Spectra are shown in FIG. 10. After about 24 h, glutathione in the sampling reservoir, but not in the fluorescence cuvette, appeared to have become exhausted by oxidation (Table 6).

TABLE 6

Summary of quantitative analysis of PEG-FVIII and PEG derivatives upon incubation of PEG-rFVIII at pH 8.5 in the presence of glutathione.

| pH 8.5 + GSH | FMOC-PEG HPLC | | DBF-PEG HPLC | | DBF-PEG 330 nm/0460-560 nm | | FMOC-PEG 330 nm/0350-355 nm | | PEG-FVIII ELISA | | FVIII:Ag ELISA | |
|---|---|---|---|---|---|---|---|---|---|---|---|---|
| H | µg/mL | % start | µg/mL | % start | Intensity | % start | Intensity | % start | ng/mL | % start | U/mL | % start |
| 0.0 | 15.3 | 100.0 | 2.3 | 100.0 | 423 | 100.0 | 702 | 100.0 | 108.1 | 100.0 | 23.7 | 100.0 |
| 1.7 | 20.0 | 130.7 | 2.8 | 121.7 | 436 | 103.2 | 649 | 92.5 | 110.8 | 102.5 | 34.7 | 146.4 |
| 3.4 | 22.8 | 149.0 | 3.1 | 134.8 | 440 | 104.1 | 602 | 85.8 | 84.6 | 78.3 | 42.8 | 180.6 |
| 5.2 | 24.8 | 162.1 | 3.1 | 134.8 | 458 | 108.2 | 594 | 84.7 | 73.3 | 67.8 | 45.7 | 192.8 |
| 7.1 | 26.0 | 169.9 | 3.1 | 134.8 | 465 | 109.9 | 578 | 82.4 | 69.8 | 64.6 | 51.1 | 215.6 |
| 22.8 | 31.4 | 205.2 | 3.6 | 156.5 | 495 | 117.0 | 614 | 87.4 | 58.8 | 54.4 | 72.9 | 307.6 |
| 31.0 | 33.5 | 219.0 | 5.7 | 247.8 | 430 | 101.6 | 543 | 77.3 | 54.3 | 50.2 | 80.1 | 338.0 |
| 47.2 | 38.4 | 251.0 | 11.4 | 495.7 | 431 | 101.9 | 519 | 73.9 | 43.0 | 39.8 | 97.4 | 411.0 |
| 53.9 | 40.1 | 262.1 | 13.6 | 591.3 | 433 | 102.4 | 504 | 71.8 | 42.2 | 39.0 | 105.1 | 443.5 |
| 71.3 | 40.3 | 263.4 | 14.8 | 643.5 | 527 | 124.6 | 538 | 76.7 | 38.4 | 35.5 | 115.8 | 488.6 |
| 78.4 | 42.0 | 274.5 | 16.0 | 695.7 | 516 | 122.0 | 474 | 67.5 | 33.3 | 30.8 | 130.5 | 550.6 |
| 94.8 | 45.5 | 297.4 | 18.2 | 791.3 | 618 | 146.2 | 509 | 72.5 | 33.0 | 30.5 | 133.3 | 562.4 |

The data in Table 6, shown as a percent of the initially measured concentrations, demonstrate the scavenging of free dibenzofulvene-PEG by reduced glutathione, as shown by the moderate increase in the specific fluorescence signal at 460-560 nm (in comparison to Example 5), and the corresponding moderate decrease of the conjugated PEG-FMOC compounds, as shown by the 350-355 nm fluorescence signal. Free FVIII antigen is generated, and FVIII-bound PEG levels decrease at a similar rate as in Example 5.

Example 9

Demonstration of the PH Effect on PEG-Dibenzofulvene Generation

Figure 11:
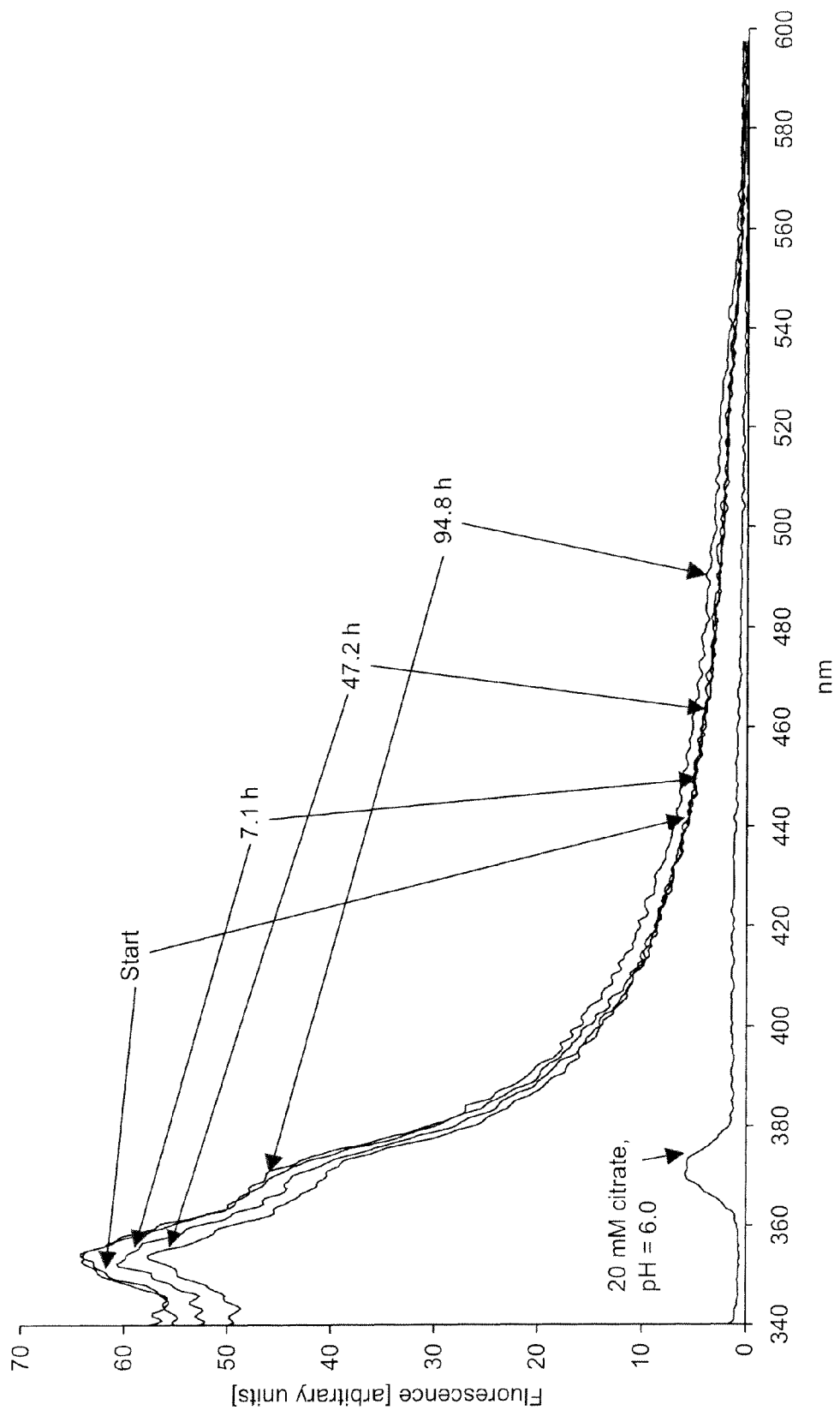
FIG. 11 shows the fluorescence spectra illustrating the stability of the PEG-FMOC-conjugate fluorescence signal (350-355 nm) upon incubation of releasable-PEGylated FVIII at pH=6.0.

The FVIII solution in Example 8 was diluted 1:5 with 20 mM citrate buffer, pH=6.0, containing 32 g mannitol, 12 g sucrose, 2.5 g $CaCl_2.2H_2O$, and 100 mg polysorbate 80 (99% oleic acid) per liter. Incubation, measurement, sampling, and analysis were carried out as set out in Example 7. Spectra are shown in FIG. 11. At pH 6.0, the release of PEG-dibenzofulvene was lower than at pH=8.5 (Compare Table 7 to Table 5). The data suggest that the mechanism of β-elimination is carried out by an attack of basic nucleophiles, such as the hydroxide anion.

VWF multimer analysis is performed by high-density horizontal SDS agarose gel electrophoresis and immunostaining using a polyclonal anti-human VWF antibody (Dako). De-polymerization of PSA-rVWF is expected to increase with increasing pH.

Example 11

In Vitro De-Polymerization of Releasable PSA-rVWF in the Presence of Primary Amines and High pH De-polymerization of a releasable water-soluble polymer-conjugate, such as a polysialic acid (PSA)-rVWF conjugate, is in another aspect carried out by increasing the amine concentration of the protein conjugate buffer. A releasable PSA-rVWF conjugate is diluted in a 0.02 M sodium citrate, 0.15 M NaCl buffer at a pH of about 9.8, containing 100 mM lysine, and incubated at 37° C. Sub-samples are withdrawn at defined time points and analyzed for their content of VWF antigen (VWF:Ag), free PSA, total PSA, and multimeric composition. Multimer analysis is carried out with high-density horizontal SDS agarose gel electrophoresis and immunostaining using antibodies either directed against human VWF (Dako, Glostrup, Denmark) or PSA (Millipore, Temecula, Calif., USA).

TABLE 7

Summary of quantitative analysis of PEG-FVIII and PEG-derivatives upon incubation of PEG-rFVIII at pH 8.5.

| pH 6.0 | FMOC-PEG HPLC | | DBF-PEG HPLC | | DBF-PEG 330 nm/0460-560 nm | | FMOC-PEG 330 nm/0350-355 nm | | PEG-FVIII ELISA | | FVIII:Ag ELISA | |
|---|---|---|---|---|---|---|---|---|---|---|---|---|
| h | μg/mL | % start | μg/mL | % start | Intensity | % start | Intensity | % start | μg/mL | % start | μg/mL | % start |
| 0.0 | 6.1 | 100.0 | 1.7 | 100.0 | 440 | 100.0 | 692 | 100.0 | 172.8 | 100.0 | 13.4 | 100.0 |
| 1.7 | 6.3 | 103.3 | 1.8 | 105.9 | 408 | 92.7 | 674 | 97.4 | 155.1 | 89.8 | 12.5 | 93.3 |
| 3.4 | 6.7 | 109.8 | 1.9 | 111.8 | 417 | 94.9 | 663 | 95.7 | 149.0 | 86.2 | 12.6 | 94.0 |
| 5.2 | 6.9 | 113.1 | 2.0 | 117.6 | 417 | 94.7 | 653 | 94.3 | 142.9 | 82.7 | 13.6 | 101.5 |
| 7.1 | 7.5 | 123.0 | 2.1 | 123.5 | 425 | 96.7 | 652 | 94.2 | 165.0 | 95.5 | 12.8 | 95.5 |
| 22.8 | 9.0 | 147.5 | 2.7 | 158.8 | 491 | 111.6 | 682 | 98.6 | 155.8 | 90.2 | 15.1 | 112.7 |
| 31.0 | 10.6 | 173.8 | 3.2 | 188.2 | 469 | 106.7 | 643 | 92.9 | 153.6 | 88.9 | 14.8 | 110.4 |
| 47.2 | 12.7 | 208.2 | 4.0 | 235.3 | 461 | 104.8 | 618 | 89.2 | 171.2 | 99.1 | 15.4 | 114.9 |
| 53.9 | 13.3 | 218.0 | 4.4 | 258.8 | 480 | 109.1 | 625 | 90.2 | 207.5 | 120.1 | 14.6 | 109.0 |
| 71.3 | 14.7 | 241.0 | 4.8 | 282.4 | 552 | 125.6 | 661 | 95.4 | 193.3 | 111.9 | 15.2 | 113.4 |
| 78.4 | 15.3 | 250.8 | 5.1 | 300.0 | 528 | 120.1 | 614 | 88.7 | 219.1 | 126.8 | 14.7 | 109.7 |
| 94.8 | 18.6 | 304.9 | 6.4 | 376.5 | 595 | 135.2 | 697 | 100.7 | 209.0 | 120.9 | 17 | 126.9 |

Example 10

In Vitro De-Polymerization of Releasable PSA-rVWF at Increased pH

De-polymerization of a releasable water-soluble polymer-conjugate, such as a polysialic acid (PSA)-rVWF conjugate, is carried out by increasing the pH of the protein conjugate. De-polymerization is measured by incubating the protein conjugate at different pH values, for example at a pH of about 6 and at a pH of about 8 or about 10. Purified PSA-rVWF is dissolved in 0.02 M Na-Citrate, 0.15 M NaCl with a pH value of about 6. For the alkaline sample, the same buffer is adjusted to increased pH of about 8 or about 10 by the addition of 0.1 M NaOH. Sub-samples are withdrawn at defined time points and analyzed regarding their content of VWF antigen (VWF:Ag), free PSA, total PSA, and VWF composition of multimers.

The content of VWF:Ag is determined with a sandwich ELISA using commercially available antibodies (Dako, Glostrup, Denmark). Free PSA and total PSA are determined by a high-performance liquid chromatography (HPLC).

Upon incubation of PSA-rVWF in the presence of the amine lysine at pH 9.8, an increase in the ratio of VWF:Ag to protein is expected over time. In addition, a majority of total PSA is expected to be released after incubation in the recited buffer. After incubation, only small amounts of PSA are expected to remain bound to the single VWF multimers.

Example 12

In Vitro Recovery of Protein Activity of Releasable PSA-rFVIII in the Presence of Selected Free Amines Protein activity of a water-soluble polymer conjugated to a protein is expected to increase in the presence of free amines, indicating the release of the polymer as amine concentration increases. In this experiment, a releasable PSA-rFVIII conjugate is diluted to 5 IU/ml FVIII chromogenic activity in a buffer with a pH of about 7.3 (10 mM histidine, 90 mM NaCl, 1.7 mM $CaCl_2$, 10 mM Tris, 0.26 mM glutathione, 176 mM mannitol, 23.5 mM trehalose, and 0.1 g/l Tween 80); the buffer additionally contains lysine, histidine, or a combination of both amino acids, and the buffer is incubated at 37° C.

to force the in vitro release of PSA from the protein conjugate. Sub-samples are withdrawn at defined time points (24 h, 48 h, and 72 h) and FVIII chromogenic activity is determined online by use of a FVIII chromogenic assay. FVIII activity is expected to increase over time in a buffer with increasing concentration of lysine, histidine, or a combination of both amines.

Example 13

In Vitro De-Polymerization of Releasable PSA-rFVIII in the Presence of a Combination of Free Amines A releasable PSA-rFVIII conjugate is incubated in a buffer (20 mM $Na_3$ citrate, 1.7 mM $CaCl_2$, 176 mM mannitol, 36 mM sucrose, and 0.1 g/l Tween 80) with a pH of 7.3; the buffer additionally contains 100 mM histidine and 100 mM lysine, and is incubated at +37° C. Alternately, the buffer is increased to a high pH (e.g. 9.8) without the addition of histidine and lysine. Sub-samples are withdrawn at defined time points up to 168 h and the functional activity of PSA-rFVIII is determined by use of a FVIII chromogenic assay (as described previously). In addition, the release of PSA is confirmed by measuring free PSA and total PSA by HPLC from frozen sub-samples. Such conditions are expected to trigger the release of PSA from the rFVIII protein in vitro.

Example 14

In Vitro De-Polymerization of Releasable PSA-rFVIII in the Presence of Hepes/Tris Previous experiments indicate that increasing the amine concentration of a buffer forces the release of a releasable water-soluble polymer from a protein conjugate. In this experiment, releasable PSA-rFVIII is incubated at 37° C. in a combination of typical amine-containing buffer substances, namely 200 mM HEPES and 200 mM Tris, at a pH of about 7.4. Sub-samples are withdrawn at defined time points. The recovery of FVIII activity is monitored by a chromogenic assay, and its ability to interact with VWF is determined. VWF binding, which critically determines survival of FVIII in the circulation, is monitored by using surface plasmon resonance technology. Using a Biacore system, various PSA-rFVIII samples are injected into the mobile phase and tested for interaction with immobilized VWF. VWF binding is expected to increase with release of PSA. Therefore, increasing chromogenic FVIII activity with time should be accompanied by an increase in rFVIII binding to VWF, which is a signal of de-polymerization (removal of PSA). As set out in previous examples, it is expected that a wide spectrum of amines can be used to force the release of PSA from such conjugates. Increases in chromogenic activity and binding to VWF indicate that functional protein is generated over time.

The invention has been described in terms of particular embodiments found or proposed to comprise preferred modes for the practice of then invention. It will be appreciated by those of ordinary skill in the art that, in light of the present disclosure, numerous modifications and changes can be made in the particular embodiments exemplified without departing from the intended scope of the invention. Therefore, it is intended that the appended claims cover all such equivalent variations which come within the scope of the invention as claimed.

What is claimed is:

1. A method of releasing a reversibly-linked water-soluble polymer from a protein modified by the water-soluble polymer comprising the step of adding free amine consisting of free lysine, histidine, or a combination thereof to a solution comprising the protein modified by the water-soluble polymer at a concentration effective to release the water-soluble polymer.

2. A method of increasing activity of a protein modified with a reversibly-linked water-soluble polymer by releasing the water-soluble polymer from the protein comprising the step of adding free amine consisting of free lysine, histidine, or a combination thereof to a solution comprising the protein modified by the water-soluble polymer at a concentration effective to release the water-soluble polymer.

3. The method of claim 1 or 2, wherein the method further comprises increasing pH of the solution comprising the protein.

4. The method of claim 3, wherein the method comprises increasing pH of the solution to about pH 10.

5. The method of claim 3, wherein the method comprises increasing pH of the solution to about 9.8.

6. The method of claim 3, wherein the method comprises increasing pH of the solution to about 8.1.

7. The method of claim 1 or 2, wherein the method further comprises increasing temperature of the solution above about 4° C.

8. The method of claim 7, wherein the temperature of the solution is increased to about 37° C.

9. The method of claim 1 or 2, wherein the method further comprises incubating the protein modified by the water-soluble polymer in the solution for at least about 5 minutes.

10. The method of claim 9, wherein the incubating step is carried out for up to about 168 hours.

11. The method of claim 9, where the incubating step is carried out for about 48 hours.

12. The method of any one of claim 1 or claim 2, wherein the protein is factor VIII (FVIII).

13. The method of any one of claim 1 or claim 2, wherein the protein is von Willebrand Factor (VWF).

14. The method of claim 1 or claim 2 wherein the water-soluble polymer is reversibly linked to the protein with 9H-(f)luoren-9-yl(m)eth(o)xy(c)arbonyl, dibenzofulvene, or a derivative thereof.

15. The method of claim 14 wherein the water-soluble polymer is linked with 9H-(f)luoren-9-yl(m)eth(o)xy(c)arbonyl, or a derivative thereof.

16. The method of any one of claims 1-6, 7-10 and 12-15, wherein the water-soluble polymer is polyethylene glycol.

17. The method of any one of claims 1-6, 7-10 and 12-15, wherein the water-soluble polymer is polysialic acid.

18. The method of claim 1 or 2, wherein the concentration of free amine is about 100 mM.

19. The method of claim 1 or 2, wherein the concentration of free amine is about 200 mM.

* * * * *